(12) United States Patent
Ueki

(10) Patent No.: US 7,893,396 B2
(45) Date of Patent: Feb. 22, 2011

(54) BIOMETRIC DEVICE AND INFORMATION TERMINAL

(75) Inventor: Hironori Ueki, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 133 days.

(21) Appl. No.: 12/174,811

(22) Filed: Jul. 17, 2008

(65) Prior Publication Data

US 2009/0039241 A1 Feb. 12, 2009

(30) Foreign Application Priority Data

Aug. 7, 2007 (JP) ............................. 2007-205122

(51) Int. Cl.
*G01J 1/42* (2006.01)
*G06K 9/00* (2006.01)

(52) U.S. Cl. ............................. 250/227.2; 250/227.14; 250/221; 600/473; 382/115

(58) Field of Classification Search ............ 250/227.11, 250/227.14, 227.2, 221, 216; 600/473, 475–477; 382/115, 116, 124, 126, 128

See application file for complete search history.

(56) References Cited

U.S. PATENT DOCUMENTS 6,182,892 B1 * 2/2001 Angelo et al. ............... 235/380

2006/0247534 A1 11/2006 Sato

FOREIGN PATENT DOCUMENTS

| JP | 07-021373 | 1/1995 |
| JP | 2005-346238 | 12/2005 |
| JP | 2006-305154 | 11/2006 |

\* cited by examiner

*Primary Examiner*—Kevin Pyo
(74) *Attorney, Agent, or Firm*—Mattingly & Malur, P.C.

(57) ABSTRACT

A compact biometric device includes a first light source for emitting light irradiated onto a subject; a first light guide whose surface is inputted with light radiated from the subject and outputs the light from the subject; a second light guide for guiding and irradiating the light emitted from the first light source onto the subject; a photo sensor to detect light output from the end of the first light guide means as a signal; a liquid crystal display installed between the subject and the surface of the first light guide; and a control unit for controlling the display on the liquid crystal display; and a signal processor unit for processing the signals detected by the photo sensor unit. The control unit controlling the liquid crystal display to change the position where light emitted from the subject is input onto the surface of the first light guide.

13 Claims, 12 Drawing Sheets

BIOMETRIC DEVICE AND INFORMATION TERMINAL

CLAIM OF PRIORITY

The present application claims priority from Japanese patent application JP 2007-205122 filed on Aug. 7, 2007, the content of which is hereby incorporated by reference into this application.

FIELD OF THE INVENTION

This invention relates to a biometric device for identifying an individual matching an image based on a biological pattern contained in the image.

BACKGROUND OF THE INVENTION

Biometrics identifies an individual by utilizing special characteristics in the biological information of the individual and has attracted attention in recent years. The biological information may be fingerprints, the iris (of the eye) or blood vessel patterns (veins), etc.

Biometrics offers the advantages of being highly convenient and secure. Biometrics is convenient and secure because no key needs to be carried and there is little threat to security from loss or illegal actions such as theft.

In biometrics, authentication by use of blood vessel patterns (vein identification) is becoming widespread. Blood vessel patterns are internal bodily information so falsification is difficult compared to fingerprints and vein authentication therefore offers higher security than fingerprints. Moreover, blood vessel (hand vein) authentication does not require irradiating light onto the pupil of the eyes such as in retinal scans. There is therefore little psychological resistance to blood vessel authentication among users and it is highly safe.

A blood vessel (or vein) authentication device is disclosed for example in JP-A-07-021373 (1995). The blood vessel authentication device irradiates near-infrared light onto the subject. The blood vessel authentication device then projects transmitted light and reflected light by utilizing an image sensor. In this case, the hemoglobin in the blood fluid absorbs most of the near-infrared rays. The blood vessel authentication device can therefore draw the vein pattern on the projected image. The blood vessel authentication device judges whether or not the vein pattern drawn in the projected image matches the pre-registered vein pattern. The blood vessel authentication device then identifies the individual based on the judgment results.

SUMMARY OF THE INVENTION

Mounting a biometric device in electronic equipment capable of being easily carried such as a cellular telephone has proven difficult due to spatial constraints in the portable electronic equipment. Biometric devices must therefore be made more compact.

Fingerprint identification devices for example, normally include sensors such as pressure sensors or contact-sensing optical image sensors to measure the fingerprint pattern. However, these types of sensors are usually the same size as a human fingertip and difficult to mount in mobile electronic equipment. Therefore, fingerprint identification devices containing miniature line sensors are being developed. These fingerprint identification devices capture an image of the finger sliding over the miniature line sensor. These fingerprint identification devices therefore had the problem of being incapable of acquiring satisfactory fingerprint images.

The blood vessel identification device on the other hand contains image sensors such as CCD (Charged Coupled Device) sensors or CMOS (Complementary Metal-Oxide Semiconductor) sensors, etc. These image sensors can be miniaturized, however the lens utilized for forming an image on the image sensor is a separate item. The blood vessel identification device therefore has the problem that reducing the size of the device is difficult.

A fingerprint identification device with a semi-transparent image sensor overlapping the liquid crystal display is disclosed in JP-A-2005-346238. In this technology, the image sensor can be installed on the liquid crystal display of a cellular telephone and so does not require a dedicated space for the image sensor. Moreover, the backlight of the liquid crystal display can be utilized unchanged as the irradiation light source during image capture.

The technology of the known art can be utilized to fabricate this semi-transparent image sensor. In the technology of the known art, the sensor array is formed by laminating layers of amorphous silicon or polysilicon on a glass substrate.

Utilizing the technology in JP-A-2005-346238 in a blood vessel (or vein) authentication device causes the following problems:

The semi-transparent image sensor is mounted on a liquid crystal display so that there is a drop in light intensity on the liquid crystal screen. This drop in light intensity causes a drop in visual recognition capability on the liquid crystal screen.

Moreover, installing the image sensor on the liquid crystal display increases the overall thickness of the liquid crystal display. The thickness of an image sensor is usually about two to three millimeters so mounting the vein authentication device on a device such as a cellular telephone with severe size limitations is difficult.

Further, increasing the photodiode sensitivity to near-infrared light to an adequate level is difficult when using photodiodes formed from polysilicon or amorphous silicon. For instance, the photodiode sensitivity generally requires increasing the thickness of the silicon film in the photodiode layer. However, a silicon film thickness from a few dozen to a few hundred nanometers is generally used due to the time required to form the silicon film and the increased cost. This type of drop in photodiode sensitivity causes a poor S/N ratio which lowers the recognition accuracy of the vein authentication device.

In view of the problems with the related art, this invention has the object of providing a space-saving biometric device with high recognition accuracy.

A typical aspect of the present invention as a biometric device for identifying individuals matching a subject based on the biological pattern of the subject in an image includes: a first light source for emitting light irradiated onto a subject; a first light guide means whose surface is input with light radiated from the subject and whose ends output the light input from the subject; a photo sensor unit to detect light output from the end of the first light guide means as a signal; a liquid crystal display unit installed between the subject and the surface of the first light guide means; a control unit for controlling the display on the liquid crystal display unit; and a signal processor unit for processing the signals detected by the photo sensor unit, and the control unit controls the display on the liquid crystal display unit so that the light emitted from the subject is input onto the surface of the first light guide unit, and the signal processor unit generates an image including the biologic pattern of the subject based on the signal detected by the photo sensor unit at each position with a change in the light input.

Another typical aspect of the present invention as a device includes: a first light source which emits light to be irradiated onto a subject; a first light guide unit which receives light radiated from the subject and which outputs the received light; a sensor unit which detects light output from the first light guide unit as a signal; a liquid crystal display unit positioned between the subject and the first light guide unit; a signal processing unit for processing said signal detected by the sensor unit, and a control unit which controls the LCD unit to permit light to pass through a first portion while preventing light from passing through a second portion, wherein the control unit changes a location of the first portion.

Yet another typical aspect of the present invention as a device includes: a first light source which emits light to be irradiated onto the subject; a liquid crystal display (LCD) unit displaying a mask image with a non-mask section; a first light guide unit that receives light from the subject that passes through the non-mask section of the mask image and which outputs the received light; a sensor unit that detects the light received from the first light guide unit; a signal processing unit for processing the signals detected by the sensor unit; and a control unit which controls a location of the non-mask section on the mask image and moves the location of the non-mask section.

The typical aspects of this invention render a biometric device that is both compact and possesses enhanced recognition accuracy.

DETAILED DESCRIPTION OF THE PREFERRED EMBODIMENTS

Figure 1:
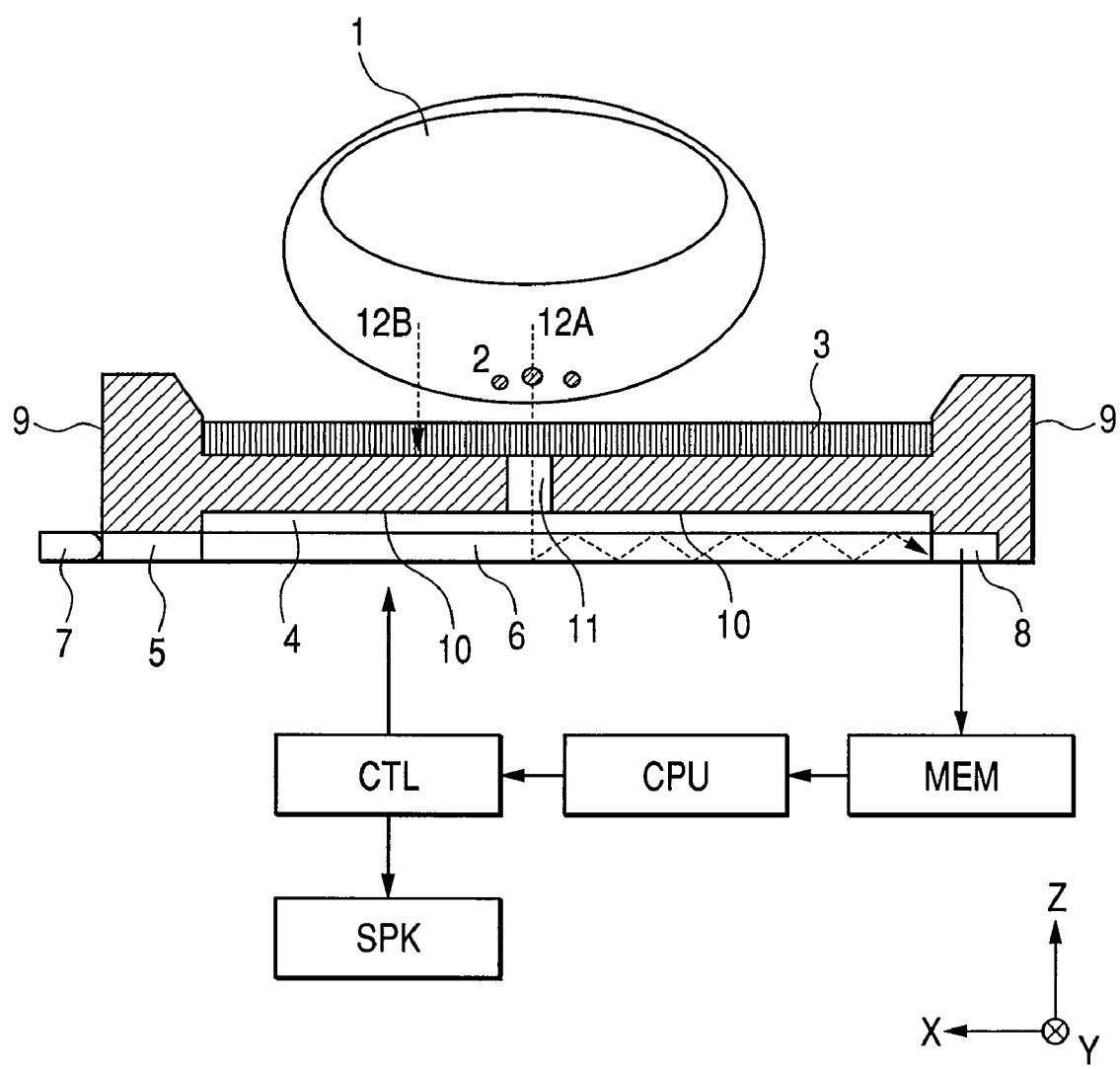
FIG. 1 is a drawing showing the structure of the biometric device of the first embodiment of this invention.

The embodiments of this invention are described next while referring to the drawings.

First Embodiment

FIG. 1 is a drawing for describing the structure of the biometric device of the first embodiment of this invention.

The biometric device authenticates the vein pattern 2 of a subject 1. The subject 1 in this embodiment is the subject's finger but may be another part of the subject's body other than a finger if an image of the vein pattern can be captured. For example, the subject 1 may be the palm of the hand or the back of the hand.

The biometric device includes: an diffusion preventive filter 3, a liquid crystal display substrate 4, a light diffusion plate 5, a light guide plate 6, a backlight source 7, a near-infrared ray light source (not shown in the drawing), a photodiode array (PD array) 8, a support frame 9, an image capture control device CTL, a memory MEM, a central processing unit CPU and a speaker SPK, etc.

In this embodiment, the X-axis is the axial direction of the subject 1. The Y-axis is the longitudinal direction of subject 1. The diffusion preventive filter 3, the liquid crystal display substrate 4 and the light guide plate 6 contains parallel surfaces on the X-Y planes. The Z-axis is the direction of the surfaces of the diffusion preventive filter 3, the liquid crystal display substrate 4 and the light guide plate 6.

The backlight source 7 is installed on one side along the X-axis of the light diffusion plate 5. The light guide plate 6 is installed along the other side along the X-axis of the light diffusion plate 5. The light guide plate 6, the liquid crystal display substrate 4 and the diffusion preventive filter 3 are installed laminated along the Z-axis.

The support frame 9 supports the diffusion preventive filter 3, the liquid crystal display substrate 4, the light diffusion plate 5, the light guide plate 6, the backlight source 7, and the PD array 8. The upper surface of the support frame 9 is installed at a position higher than the upper surface of the diffusion preventive filter 3. This placement actively prevents contact between the subject 1 and the diffusion preventive filter 3 that might apply pressure on the veins 2 of the subject 1. The biometric device can therefore capture sharp images of the vein 2 pattern of subject 1.

The backlight source 7 emits white-colored light. The backlight source 7 for example contains LED (Light Emission Photodiodes) components of the known art. The white-colored light emitted by the backlight source 7 is utilized as a backlight for displaying letters and images on the liquid crystal display substrate 4. The light emission timing of the backlight source 7 is described in FIG. 11.

The light diffusion plate 5 is for example an acrylic plate of the known art. The light diffusion plate 5 diffuses the white-colored light emitted from the backlight source 7 uniformly towards the X-Y plane. The white-colored light diffused by the light diffusion plate 5 is then irradiated onto the edge of the light guide plate 6.

The light guide plate 6 is for example an acrylic plate of the known art. Reflective dots (not shown in drawing) are printed on the bottom surface of the light guide plate 6.

The light guide plate 6 diffuses the white-colored light irradiated from the light diffusion plate 5 uniformly towards the X-axis. Moreover among this diffused white-colored light, the light guide plate 6 outputs white-colored light randomly reflected by the reflective dots towards the Z-axis. The light guide plate 6 in this way irradiates light emitted from the backlight source 7 onto the liquid crystal display substrate 4.

A portion of the near-infrared light output from the surface of the subject 1 on the other hand, transmits through the diffusion preventive filter 3 and the liquid crystal display substrate 4 and irradiates onto the surface of the light guide plate 6. When the backlight source 7 is off, the light guide plate 6 guides the light towards the X-axis, after the near-infrared light that was input is randomly reflected by the reflective dots. The light guide plate 6 therefore irradiates the near-infrared light (that was irradiated from the surface of the applicable light guide plate 6) onto the PD array 8 by emitting it from the edge of the applicable light guide. The PD array 8 detects the near-infrared light emitted from the light guide plate 6. The structure of the light guide plate 6 is described in detail later using FIG. 8.

The liquid crystal display substrate 4 includes a TFT (Thin Film Transistor) drive substrate, polarizing filter, transparent electrode, liquid crystal layer and color filter, etc. The liquid crystal display substrate for example of the known art containing multiple pixels is utilized for the liquid crystal display substrate 4. The color filter however besides being transparent to RGB colored light, must also be transparent to the near-infrared light that is output from the surface of the subject 1.

The amount of transparent light in the liquid crystal layers on the liquid crystal display substrate 4 is regulated in each pixel by controlling the voltage applied to the liquid crystal layers.

The liquid crystal display substrate 4 also includes a display function and a mask function. The display function displays images and characters, etc.

The mask function controls the areas on the surface of light guide plate 6 where near-infrared light output from the surface of the subject 1 is input onto the light guide plate 6. The liquid crystal display substrate 4 for example displays a mask image including the mask section 10 and the non-mask section 11. The mask section 10 is a section displayed in black. The black display is a state set to allow the lowest transmittance of near-infrared light. The mask section 10 therefore allows almost no near-infrared light to pass through.

The non-mask section 11 on the other hand is displayed in white. The white display is the section set for the highest near-infrared ray transmittance. Almost all of the near-infrared light therefore transmits through the non-mask section 11.

The mask section 10 blocks a portion of the near-infrared light 12b emitted from the surface of subject 1 to prevent irradiation onto the surface of the light guide plate 6. A portion of the near-infrared light 12B emitted from the surface of the subject 1 however is irradiated onto the surface of the light guide plate 6 after transmitting through the non-mask 11, and is detected by the PD array 8.

The PD array 8 in other words, detects near-infrared light output from the surface of the subject 1 in the vicinity of the non-mask section 11. Shifting the non-mask section 11 allows shifting the position where near-infrared light is detected by the PD array 8 among positions on the subject 1 emitting the near-infrared light. A two-dimensional image can therefore be captured by shifting the PD array 8 detection position along the Y-axis, while shifting the non-mask section 11 along the X-axis. Most of the near-infrared light is absorbed by hemoglobin in the blood fluid. The vein 2 pattern of the subject 1 is therefore drawn on the captured image.

The PD array 8 is formed as an array of photodiodes (PDs) along the Y-axis (primary direction) on the silicon substrate in a line sensor shape. The light input area of the PDs in the PD array 8 formed on the side surface of the PD array 8 contains individual PDs that detect near-infrared light input from the light guide plate 6.

The PD array 8 connects to a signal readout circuit and an A/D converter, etc. The signal readout circuit and an A/D converter are technology of the known art. The signal readout circuit therefore loads (reads) signals detected by the PD array 8. The AD converter converts the signals read out by the signal readout circuit into digital signals.

Many tiny matrices are formed in the diffusion preventive filter 3. The diffusion preventive filter 3 in this way blocks the light that was input diagonally onto the substrate (X-Y plane) of diffusion preventive filter 3. The diffusion preventive filter 3 for example functions as a matrix grid of the known art to serve as an anti-exposure filter.

The light that transmitted through the diffusion preventive filter 3 possesses directivity. A drop in spatial resolution in the captured image can therefore be prevented even if there is a spatial gap between the subject 1 and the diffusion preventive filter 3.

The biometrics device may contain a filter with a structure different from the diffusion preventive filter 3. The filter may be any structure provided that blocks light input diagonally onto the X-Y plane. The other exemplary filters include a microlens array of the known art or an optical fiber plate of the known art, etc.

The biometrics device need not include a diffusion preventive filter 3. However in that case, the subject 1 and the liquid crystal display substrate 4 must be placed in contact with each other or in sufficient proximity to each other.

The image capture control device CTL controls the turning on and turning off of the backlight source 7 according to instructions from the central processing unit CPU. The image capture control device CTL controls the turning on and off of the near-infrared ray light source (not shown in drawing) according to instructions from the central processing unit CPU. The infrared ray light source is described in detail using FIG. 7.

The image capture control device CTL controls the display such as characters and images from the liquid crystal display substrate 4. The image capture control device CTL controls the display of mask images from the liquid crystal display substrate 4.

The image capture control device CTL also controls the detecting of near-infrared light by the PD array 8.

The memory MEM stores the signals detected by the PD array 8. The central processing unit CPU generates two-dimensional images (captured images) based on the detected signals recorded in the memory MEM. The captured images are drawn on the vein pattern of the subject 1.

The central processing unit CPU implements biometric authentication based on the captured images. The biometric authentication method is disclosed for example in JP-A-07-021373 (1995).

More specifically, the central processing unit CPU judges whether or not the vein pattern drawn in the captured image matches the pre-stored vein pattern. The central processing unit CPU then authenticates the individual based on the applicable judgment results.

The central processing unit CPU next instructs the image capture control device CTL to output the authentication results. The image capture control device CTL thereupon outputs the authentication results to at least one from among the liquid crystal display substrate 4 and the speaker SPK.

The biometric device of this invention may be mounted in any information terminal containing a liquid crystal screen. Information terminals mounted with the biometric device may include cellular telephones, PDA (Personal Digital Assistant), electronic notebooks, automobiles, personal computers, digital cameras, and digital video cameras or bank ATMs, etc.

If the biometric device is mounted in an information terminal then all or any portion among the memory MEM, central processing unit CPU and speaker SPK may be jointly utilized with the components contained in the applicable information terminal.

Figure 2:
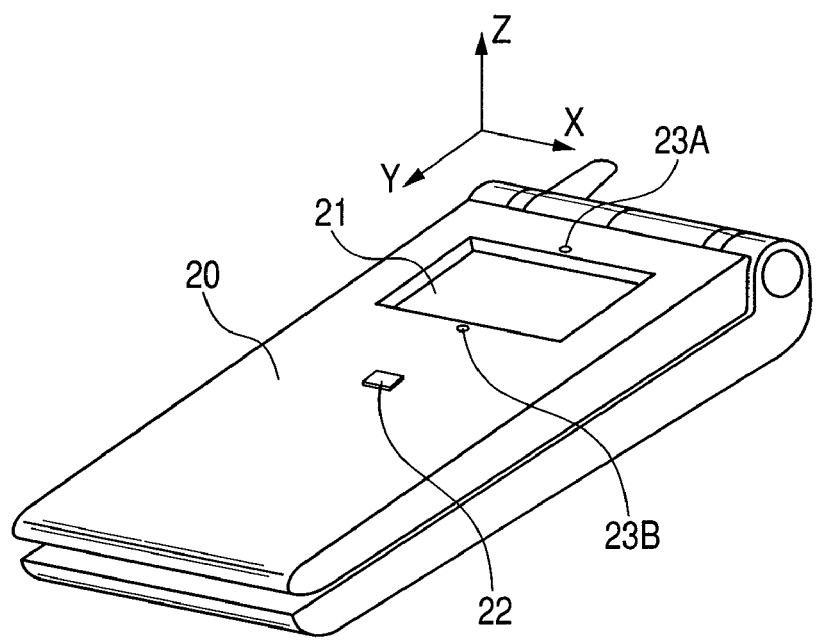
FIG. 2 is a drawing showing the outer appearance of the cellular telephone mounted with the biometric device of the first embodiment of this invention.

FIG. 2 is a drawing showing the outer appearance of the cellular telephone 20 in which the biometric device 21 of the first embodiment of this invention is mounted.

The cellular telephone 20 of this invention is the fold-up type and includes a main display and a sub-display. This cellular telephone 20 may be a one piece type and need not be the fold-up type. In other words, the cellular telephone 20 may be any type provided it includes a display.

In the example in the present embodiment, the sub-display in the cellular telephone 20 is also utilized as the biometric device 21. The biometric device 21 may utilize the main display in the cellular telephone 20 rather than the sub-display of the cellular telephone 20.

A start switch 22 and electrodes 23A and 23B are mounted in the exterior of the cellular telephone 20.

The electrodes 23A and 23B are utilized for detecting the placement of the subject 1 on the biometric device 21. The electrodes 23A and 23B are therefore installed on the periphery of the sub-display in the cellular telephone 20.

More specifically, a slight difference in the voltage potential is rendered between the electrodes 23A and 23B by a power supply (not shown in drawing). If the subject 1 is in position, then a current flows by way of the subject 1 between the electrode 23A and electrode 23B. The biometric device 21 detects the placement on the subject 1 by measuring the electrical current flowing between the electrode 23A and electrode 23B.

The start switch 22 receives an instruction from the user to start biometric authentication.

Figure 3:
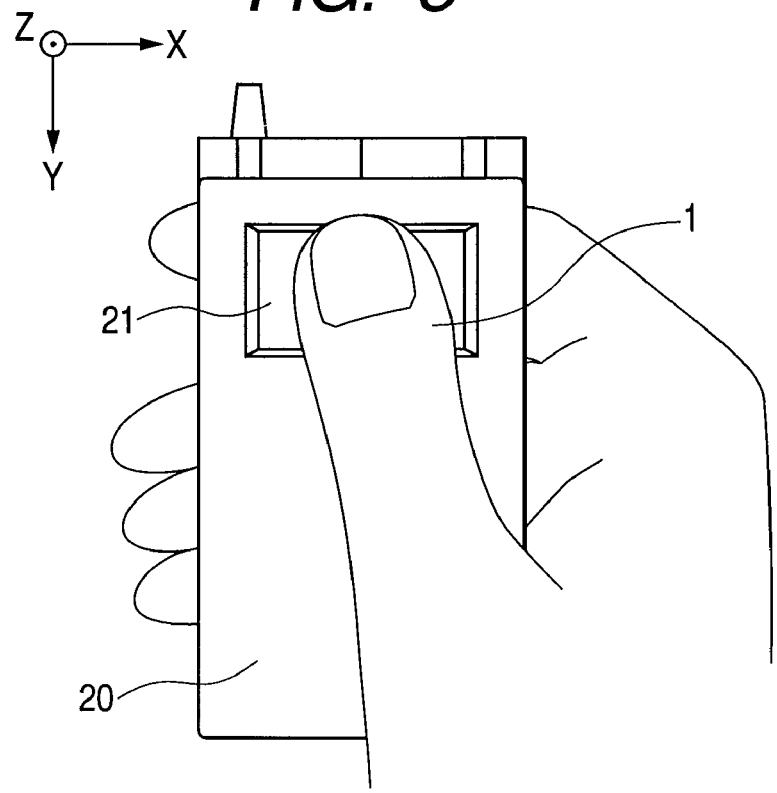
FIG. 3 is drawing showing the placement of the subject on the biometric device of the first embodiment of this invention.

FIG. 3 is drawing showing the placement of the subject (thumb) 1 on the biometric device 21 of the first embodiment of this invention.

The subject 1 is positioned so as to simultaneously contact the two electrodes 23A and 23B. The subject 1 placement however causes fluctuations during each authentication. The biometric device 21 of this embodiment can capture a sharp image of the vein 2 pattern of the subject 1 regardless of how the subject 1 is positioned.

In the example used in this embodiment, the thumb of the right of subject 1 was utilized however other fingers of the left hand or right hand may also be utilized.

Figure 4:
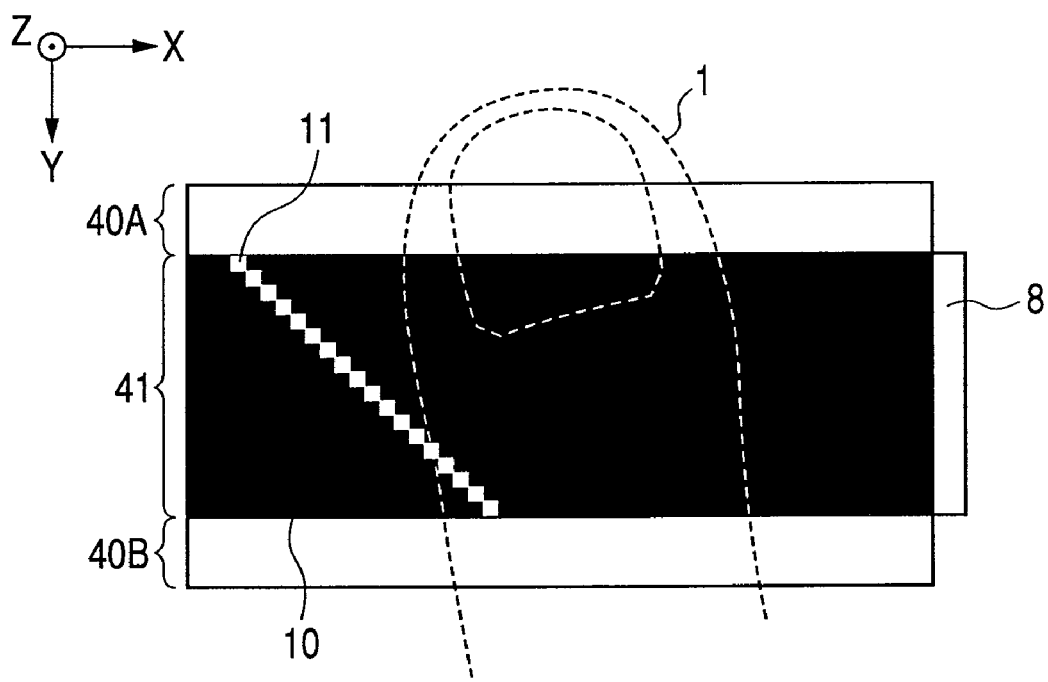
FIG. 4 is a drawing showing an example of the mask image displayed on the liquid crystal display substrate of the biometric device of the first embodiment of this invention.

FIG. 4 is a drawing showing an example of the mask image displayed on the liquid crystal display substrate 4 of the biometric device 21 of the first embodiment of this invention.

The mask image includes a near-infrared ray irradiation section 40A and 40B, and also a display-detector section 41.

The near-infrared ray irradiation section 40A is an area formed on the upper section along the Y-axis. The near-infrared ray irradiation section 40B is an area formed on the lower section along the Y-axis. The near-infrared ray irradiation sections 40A and 40B are displayed in white during image capture. The near-infrared light irradiated from the lower section of the liquid crystal display substrate 4 passes through the near-infrared ray irradiation sections 40A and 40B and irradiates onto the subject 1.

The near-infrared light irradiated onto the subject 1 repeatedly transmits through and scatters in the interior of the subject 1. A portion of the near-infrared light irradiated onto the subject 1 is then output from the surface of the subject 1.

The display-detector section 41 is an area formed in the center section along the Y-axis. The display-detector section 41 includes a mask section 10 and a non-mask section 11. The mask section 10 is displayed in black. The non-mask section 11 is displayed in white.

The mask section 10 blocks a portion of the near-infrared light emitted from the surface of subject 1, which does not irradiate onto the surface of the light guide plate 6. On the other hand, a portion of the near-infrared light emitted from the surface of the subject 1 irradiates onto the light guide plate 6 after passing through the non-mask section 11, and is detected by the PD array 8.

Each dot is located at a respective position along the Y-axis in the non-mask section 11. The dots make up one or more display pixels. The dots can, for example, be made up of 2×2 display pixels or 3×3 display pixels.

The dots are preferably not placed adjacent to other dots in the X-axis direction and the Y-axis direction. If the dots are placed adjacent to each other then light might diffuse among the adjacent dots causing a drop in spatial resolution in the captured image. This phenomenon is described in detail using FIG. 10.

The dots making up the non-mask section 11 for the mask image shown in FIG. 4 for example are positioned obliquely along the X-Y plane.

The biometric device 21 moves each dot position in sequence along the X-axis during image capture. The biometric device 21 in this way moves the dots to all positions along the X-axis. The PD array 8 then measures the irradiated light intensity at the respective positions where the dots were moved.

Since one dot each is placed at the respective positions along the Y-axis, the central processing unit CPU can form a two-dimensional image (captured image) on the non-mask section 11 based on the irradiate light intensity measured by the PD array 8. The CPU draws a vein pattern 2 of the subject 1 in the captured image.

The dot size is set according to the spatial resolution required for the captured image. A typical pitch for display pixels of the liquid crystal display substrate 4 arranged in an array along the X-axis and along the Y-axis is 50 micrometers (μm). A typical size for dots making up the 2×2 display pixels along the X-axis and along the Y-axis is respectively 100 micrometers (μm).

Figure 5:
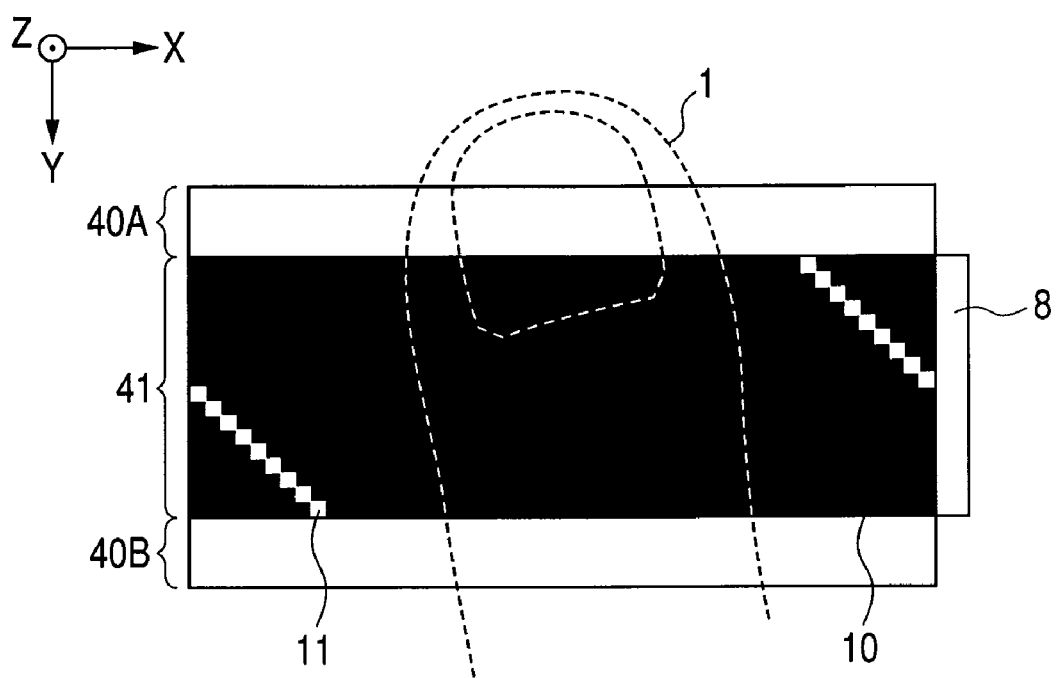
FIG. 5 is a drawing showing an example of the mask image displayed on the liquid crystal display substrate of the biometric device of the first embodiment of this invention.

FIG. 5 is a drawing showing an example of the mask image displayed on the liquid crystal display substrate 4 of the biometric device 21 of the first embodiment of this invention.

In the mask image in FIG. 5, the dots making up the non-mask section 11 contained in the mask image of FIG. 4 are being moved. The biometric device 21 moves each of the dots making up the non-mask section 11 in sequence along the X-axis. The biometric device 21 however moves dots that reached one edge of the X-axis, towards the other edge of the X-axis. By repeating this action, the biometric device 21 moves each dot to all positions along the X-axis. Then, after moving the dots to all positions along the X-axis, the biometric device 21 then terminates the dot movement.

Figure 6:
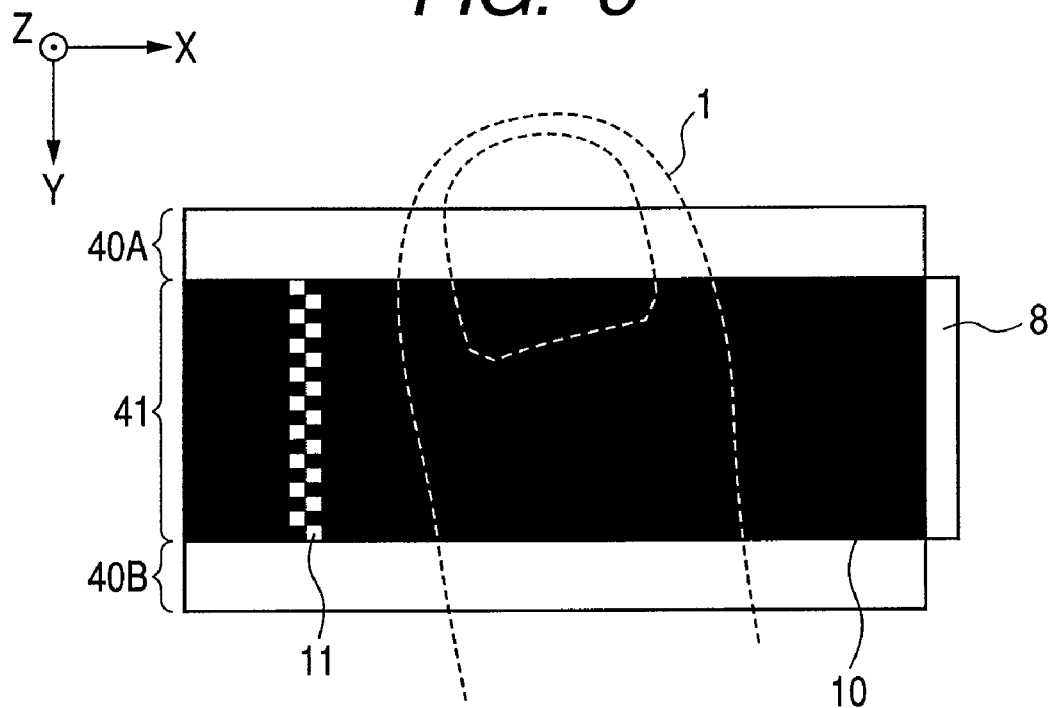
FIG. 6 is a drawing showing another example of the mask image displayed on the liquid crystal display substrate of the biometric device of the first embodiment of this invention.

FIG. 6 is a drawing showing an example of the mask image displayed on the liquid crystal display substrate 4 of the biometric device 21 of the first embodiment of this invention.

The biometric device 21 may display the mask image shown in FIG. 6 instead of the mask image shown in FIG. 4. The X-axis positions of the dots making up the non-mask section 11 shown in FIG. 6 are replaced one line each.

Namely, any dot placement is allowed in the mask image on the non-mask unit 11 if one dot each is placed at respective positions along the Y-axis. In other words, the placement of dots making the non-mask section 11 may be any placement beyond the placements shown in FIG. 4 and FIG. 6. The dots are preferably placed so as not to adjacently contact other dots on the X-axis and the Y-axis.

Even in the case of the mask image shown in FIG. 6, the biometric device 21 moves the dots making up the non-mask section 11 in order, along the X-axis. The biometric device 21 however moves dots that reached one edge of the X-axis, towards the other edge of the X-axis. By repeating this action, the biometric device 21 moves each dot to all positions along the X-axis. Then, after moving the dots to all positions along the X-axis, the biometric device 21 then terminates the dot movement.

Figure 7:
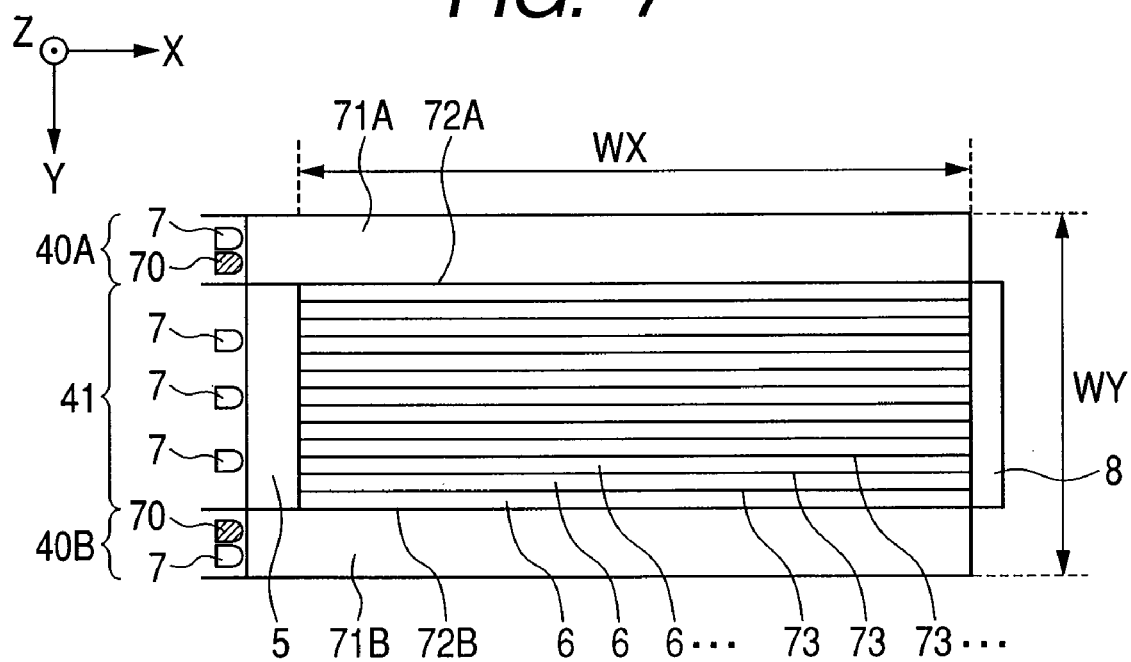
FIG. 7 is a drawing showing the structure of the biometric device of the first embodiment of this invention.

FIG. 7 is a drawing showing the structure of the biometric device 21 of the first embodiment of this invention.

This explanatory drawing shows the placement of the light diffusion plate 5, the light guide plate 6, the backlight source 7, the PD array 8, the light guide plates 71A, 71B, and the near-infrared ray light source 70.

The area WX along the X-axis and the area WY along the Y-axis in FIG. 7 are equivalent to the display area in the liquid crystal display substrate 4.

A light guide plate 71A is positioned directly below the area shown in the near-infrared ray irradiation section 40A of the mask image, among the areas displayed on the liquid crystal display substrate 4. In the liquid crystal display substrate 4 area, a light guide plate 71B is installed in the same way directly below the area displayed in the near-infrared ray irradiation section 40B of the mask image. The backlight sources 7 and near-infrared ray light source 70 are positioned on the side edge along the X-axis of 71B and light guide plate 71A.

The light guide plates 71A and 71B are made for example from acrylic and are technology of the known art. Reflective dots (not shown in drawing) are printed on the bottom surface of the light guide plate 71A and 71B.

The light guide plates 71A and 71B diffuse the white light emitted from the backlight source 7 and the near-infrared light emitted from the near-infrared light ray source 70 uniformly towards the X-Y plane. Moreover, among this diffused white light and near-infrared light, the light guide plates 71A and 71B output the white light and near-infrared light scattered by the dots, towards the Z-axis. The light guide plates 71A and 71B in this way irradiate a backlight onto the liquid crystal display substrate 4, when the liquid crystal display substrate 4 is displaying characters and images. The light guide plates 71A and 71B irradiate near-infrared light onto the subject 1 during capture of the image.

A partition wall 72A is installed on the side surface along the Y-axis of light guide plate 71A. A partition wall 72B is installed in the same way on the side surface along the Y-axis of light guide plate 71B. The partition walls 72A and 72B are made from material that does not allow light to transmit through. The partition walls 72A and 72B are made from example from a metallic film layer of the known art. The partition walls 72A and 72B therefore prevent light from diffusing onto the light guide plate 6.

Multiple light guide plates 6 are installed directly below the display-detector section 41 in the area displayed on the mask image in the display area in the liquid crystal display substrate 4. The light guide plates 6 are formed in strips longitudinally along the X-axis. A partition wall 73 is installed on the side surface along the Y-axis of the light guide plates 6. The partition wall 73 is identical to the partition walls 72A and 72B. The partition wall 73 prevents light from diffusing onto the other light guide plates 6, 71A, and 71B.

The size of one light guide plate 6 along the Y-axis corresponds to the size of the dots along the Y-axis in the non-mask section 11. A typical size for one light guide plate 6 along the Y-axis is 100 micrometers (μm). Moreover one guide plate 6 is installed directly beneath the dots in the non-mask section 11.

A light diffuser plate 5 is installed on one side surface along the X-axis of light guide plate 6. A PD array 8 is installed on the other side surface along the X-axis of light guide plate 6. One photodiode among the photodiodes making up the PD array 8 is installed for each single light guide plate 6.

A background light source 7 is installed on the side surface of the light diffuser plate 5.

The light diffuser plate 5 diffuses the white light emitted from the backlight source 7 uniformly along the X-Y plane. The white light diffused by the light diffuser plate 5 irradiates onto the edge of the light guide plate 6.

The light guide plate 6 diffuses white light emitted from the light diffuser plate 5 uniformly along the X-axis. Among this diffused white light, the light guide plate 6 outputs white light scattered (or randomly reflected) by the reflective dots, along the Z-axis. The light guide plate 6 in this way irradiates backlight onto the liquid crystal display substrate 4, when the liquid crystal display substrate 4 is displaying characters and images.

The biometric device 21 turns off the backlight source 7 and turns on the near-infrared ray light source 70 during image capture. The light guide plates 71A and 71B then uniformly diffuses the near-infrared light emitted from the near-infrared ray light source 70, along the X-Y plane. Moreover, among this diffused near-infrared light, the light guide plates 71A and 71B output near-infrared light scattered (randomly reflected) by the reflective dots, along the Z-axis. The light guide plates 71A and 71B in this way irradiate near-infrared light onto the subject 1 during image capture.

The near-infrared light irradiated onto the subject 1 repeatedly transmits through and scatters in the interior of the subject 1. A portion of the near-infrared light irradiated onto the subject 1 is then output from the surface of the subject 1. The near-infrared light output from the surface of the subject 1, transmits through the dots contained in the non-mask section 11 of the mask image displayed in the liquid crystal display substrate 4, and irradiates onto the surface of light guide plate 6. After the near-infrared red light is randomly reflected by the reflective dots, the light guide plate 6 guides it along the X-axis. In other words, the light guide plate 6 irradiates the near-infrared light input from the surface of the applicable light guide plate 6, onto the PD array 8. The PD array 8 then detects the near-infrared light that was input from the light guide plate 6.

The near-infrared light input from the light guide plate 6 is detected in parallel from each light guide plate 6 by the PD array 8.

Figure 8:
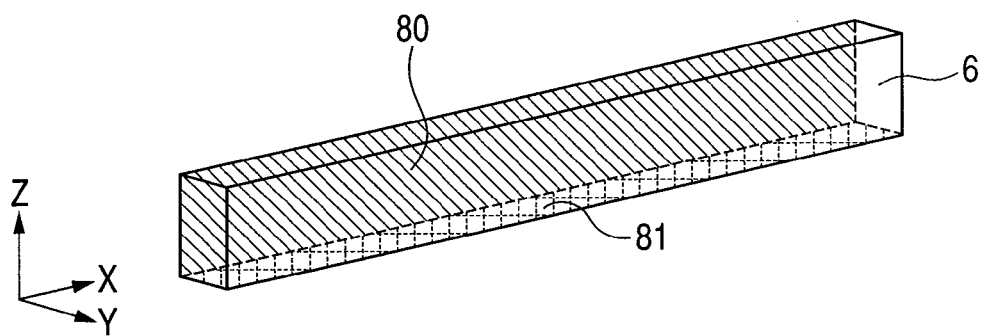
FIG. 8 is a perspective view showing the light guide plate in the biometric device of the first embodiment of this invention.

FIG. 8 is a perspective view showing the light guide plate 6 in the biometric device 21 of the first embodiment of this invention.

The light guide plate 6 is for example an acrylic plate of the known art. Reflective dots are printed on the bottom surface of the light guide plate 6. Light striking the reflective dots printed on the bottom surface 81 are scattered and output along the Z-axis.

A partition wall 73 is formed on the side surface 80 of the light guide plate 6. The partition wall 73 is made for example from a metallic film of the known art coated on the side surface of light guide plate 6. The partition wall 73 does not transmit light and therefore prevents light from diffusing along the Y-axis.

Figure 9:
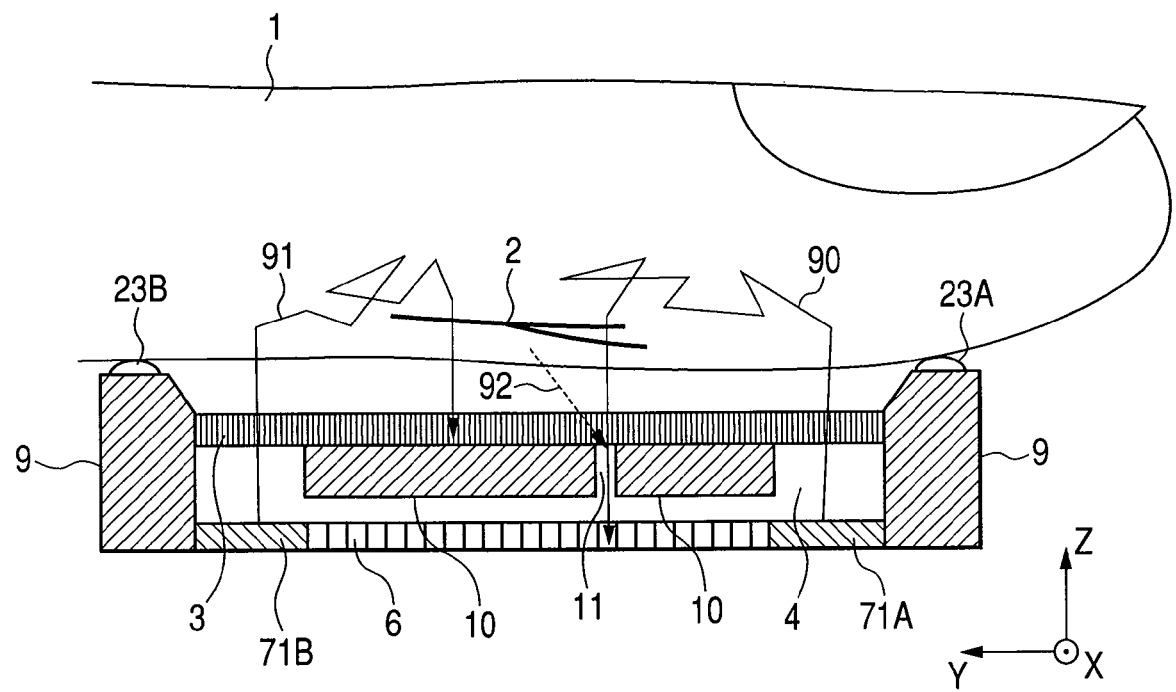
FIG. 9 is a cross sectional view along the Y-Z plane of the biometric device of the first embodiment of this invention.

FIG. 9 is a cross sectional view along the Y-Z plane of the biometric device 21 of the first embodiment of this invention.

The light guide plates 71A and 71B output the near-infrared light emitted from the near-infrared ray light source 70 along the Z-axis during capturing of the image. The light guide plates 71A and 71B in this way irradiate near-infrared light onto the subject 1.

The near-infrared light irradiated onto the subject 1, repeatedly transmits through and scatters in the interior of the subject 1. A portion of the near-infrared light 90 irradiated onto the subject 1 is then output from the surface of the subject 1. A portion of the near-infrared light 90 output from the surface of the subject 1, transmits through the dots contained in the non-mask section 11 of the mask image displayed in the liquid crystal display substrate 4, and irradiates onto the surface of light guide plate 6. After the near-infrared light 90 input from the surface of the applicable light guide plate 6 is randomly reflected by the reflective dots, the light guide plate 6 guides it along the X-axis. The light guide plate 6 in this way, irradiates the near-infrared light 90 input from the surface of the applicable light guide plate 6, onto the PD array 8. The PD array 8 then detects the near-infrared light 90 that was input from the light guide plate 6.

A portion of the near-infrared light 91 output from the surface of the subject 1 on the other hand, is blocked by the mask section 10 for the mask image displayed on the liquid crystal display substrate 4 and so is not detected by the PD array 8.

The near-infrared light 92 output from the surface of the subject 1 diagonally towards the liquid crystal display substrate 4 is blocked by the diffusion preventive filter 3 and so is not detected by the PD array 8. A drop in the spatial resolution of the captured image is prevented in this way.

Figure 10:
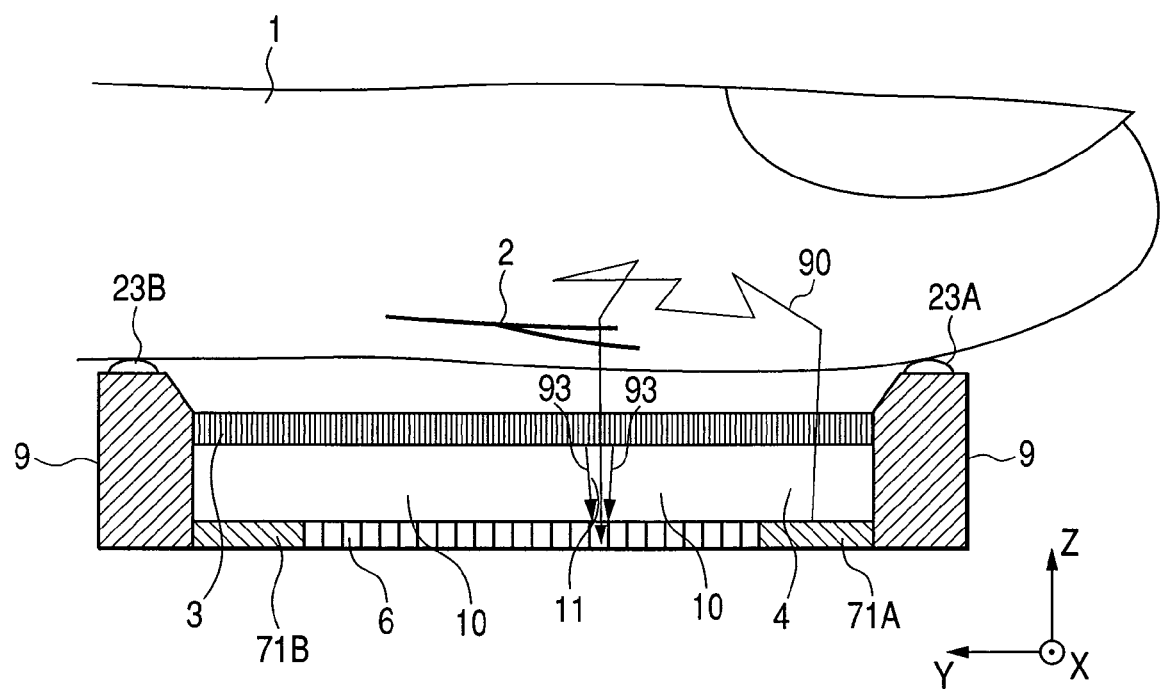
FIG. 10 is a cross sectional view along the Y-Z plane of the biometric device of the first embodiment of this invention.

FIG. 10 is a cross sectional view along the Y-Z plane of the biometric device 21 of the first embodiment of this invention.

FIG. 10 shows the multiple dots contained in the non-mask section 11 of the mask image, when the dots are adjacent to each other along the Y-axis.

In this case, rather than just the near-infrared light 90, the near-infrared light 93 scattered among the adjacent dots is also input to the light guide plate 6. A drop in the spatial resolution therefore occurs in the captured image. So to prevent in the decrease in spatial resolution, the dots in the non-mask section 11 are preferably placed so as not to be adjacent to other dots along the X-axis and along the Y-axis.

Figure 11:
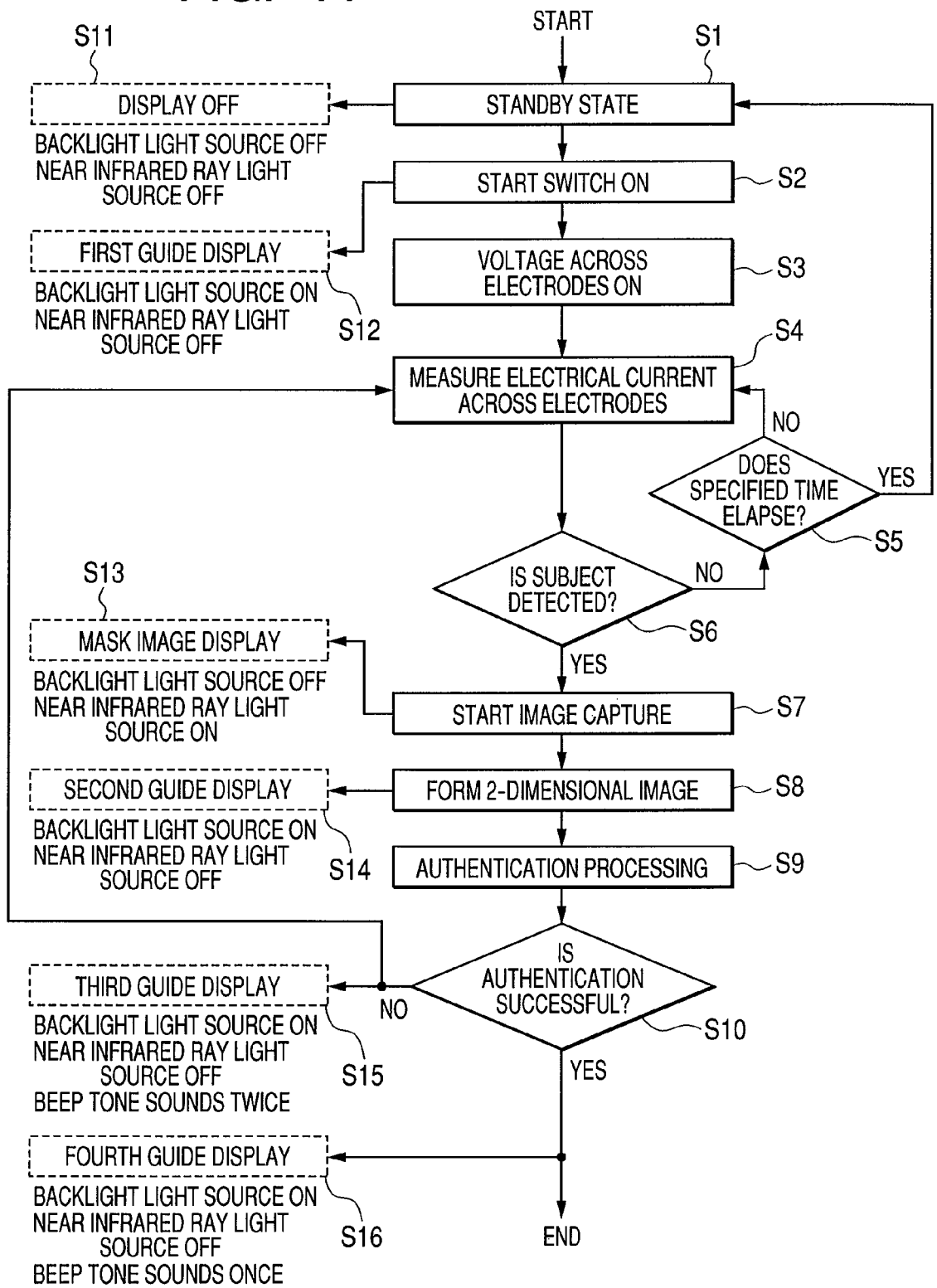
FIG. 11 is a flow chart showing the processing in the biometric device of the first embodiment of this invention.

FIG. 11 is a flow chart showing the processing in the biometric device 21 of the first embodiment of this invention.

The steps shown by the dashed line in this flow chart shows the state of the screen displayed on the liquid crystal display substrate 4. The screen appearing on the liquid crystal display substrate 4 is maintained in that state until changed in the following screen. The central processing unit CPU implements the processing in the biometric device 21.

The biometric device 21 is first of all set to standby until the start switch S22 is operated (S1). Nothing is displayed on the liquid crystal display substrate 4 at this time (S11). The backlight source 7 and the near-infrared ray light source 70 are therefore turned off.

When the start switch S22 is then operated (S2), the biometric device 21 applies a voltage across the electrode 23A and the electrode 23B (S3). The biometric device 21 at this time displays a first guide screen shown in FIG. 12, onto the liquid crystal display substrate 4 (S12). The biometric device 21 then turns on only the backlight source 7 along with the display on the first guide screen. The near-infrared ray light source 70 in other words remains off.

Figure 12:
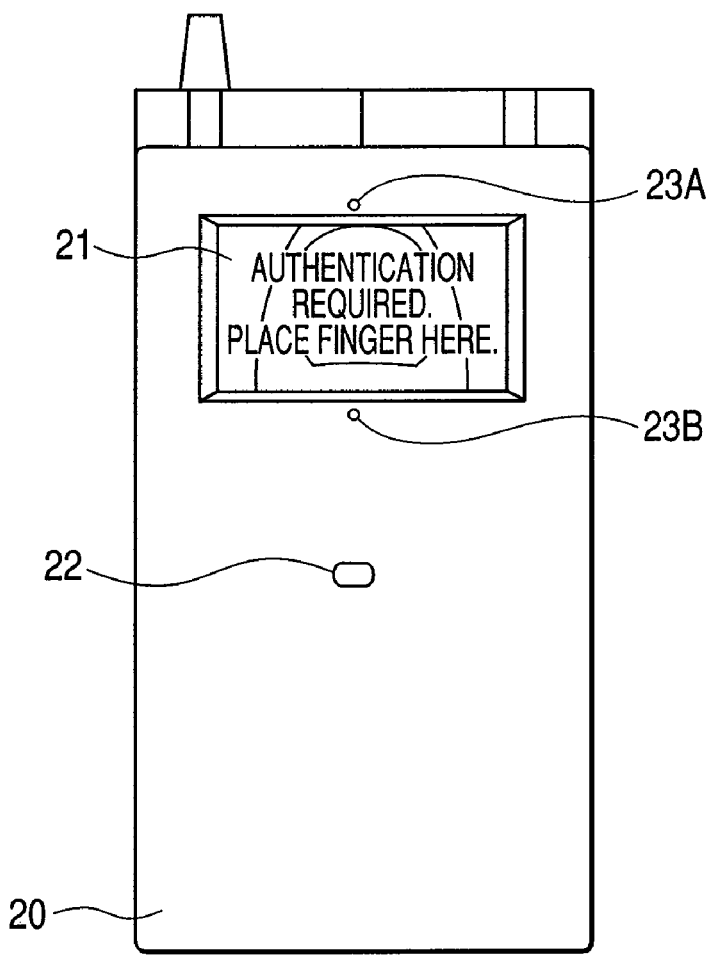
FIG. 12 is a drawing showing a first guide screen displayed on the biometric device during the start of authentication in the first embodiment of this invention.

FIG. 12 is a drawing showing a first guide screen displayed on the biometric device 21 during the start of authentication in the first embodiment of this invention.

The biometric device 21 specifies the subject 1 placement to the user by displaying the first guide screen. The first guide screen may also show the subject 1 placement position. The subject 1 placement accuracy is in this way improved so that the rate of biometric recognition errors by the biometric device 21 can be reduced.

The process here returns to FIG. 11.

The biometric device 21 measures the electrical current value across the electrode 23A and the electrode 23B after applying a voltage across the electrode 23A and the electrode 23B (S4). The biometric device 21 then decides whether or not the subject 1 placement was detected based on the electrical current value that was measured (S6).

When the subject 1 placement was not detected, the biometric device 21 next judges whether the specified time elapsed after the start switch 22 was operated. This specified time is, for example, 30 seconds.

If the biometric device 21 judges that the specified time has elapsed, then the process returns to step S1 and sets to standby.

On the other hand, if judged that the specified time has not elapsed then the biometric device 21 returns to step S4, and re-measures the electrical current across electrode 23A and the electrode 23B.

However if the subject 1 placement was detected in step S6, then the biometric device 21 starts the image capture of the subject 1 (S7).

During image capture, the biometric device 21 displays the mask image (S13). The biometric device 21 at this time turns the backlight source 7 off and the near-infrared ray light source 70 on. The biometric device 21 then measures the light intensity input from the light guide plate 6 to the PD array 8 at each light guide plate 6.

During image capture, the biometric device 21 moves each dot position contained in the non-mask section 11 of the mask image, in sequence along the X-axis. The biometric device 21 in this way moves each dot to all positions along the X-axis. The biometric device 21 measures the intensity of the light input from light guide plate 6 to the PD array 8 at each position where the dot was moved.

The biometric device 21 in this way measures the intensity of the light transmitting through the dots that irradiated onto the PD array 8 from each light guide plate 6.

The biometric device 21 next forms a two-dimensional image (image capture) based on the input light intensity that was measured at each dot (S8).

The biometric device 21 then authenticates the pattern based on the captured image (S9). More specifically, the biometric device 21 judges whether or not the vein pattern drawn on the captured image matches the pre-registered vein pattern. The biometric device 21 then authenticates the individual based on the applicable judgment results.

Figure 13:
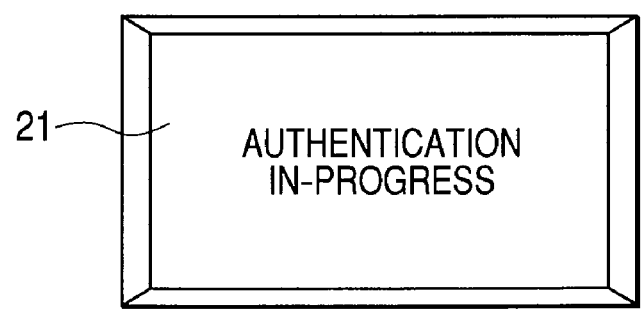
FIG. 13 is a drawing showing a second guide screen displayed on the biometric device during the authentication processing and image forming in the first embodiment of this invention.

The biometric device 21 displays the second guide screen shown in FIG. 13 on the liquid crystal display substrate 4 during the authentication processing in step S9 and the forming of the image in step S8 (S14). The biometric device 21 at this time turns off the near-infrared ray light source 70, and turns on the backlight source 7.

FIG. 13 is a drawing showing a second guide screen displayed on the biometric device 21 during the authentication processing and image forming in the first embodiment of this invention.

The biometric device 21 notifies the user that authorization is in progress by displaying the second guide screen.

The description here returns to FIG. 11.

The biometric device 21 judges whether or not the authorization succeeded in the authorization process in step S9 (S10).

If the authorization failed then the biometric device 21 returns to step S4 and repeats the process. The biometric device 21 at this time displays the third guide screen shown in FIG. 14 on the liquid crystal display substrate 4 (S15). The biometric device 21 at this time keeps the near-infrared ray light source 70 turned off and the backlight source 7 turned on.

The biometric device 21 simultaneously notifies the user that authorization failed by a method such as sounding two beep tones, which is different from the method for notifying that authorization succeeded. The user is in this way notified that authorization failed while the user's finger is still placed on the biometric device 21.

Figure 14:
FIG. 14 is a drawing showing a third guide screen displayed on the biometric device when authentication failed in the first embodiment of this invention.

FIG. 14 is a drawing showing the third guide screen displayed on the biometric device 21 when authentication failed in the first embodiment of this invention.

The biometric device 21 notifies the user that authentication failed by displaying the third guide screen, and instructs the user the place the subject 1 (finger). The third guide screen may display the subject 1 placement position.

The description here returns to FIG. 11.

Figure 15:
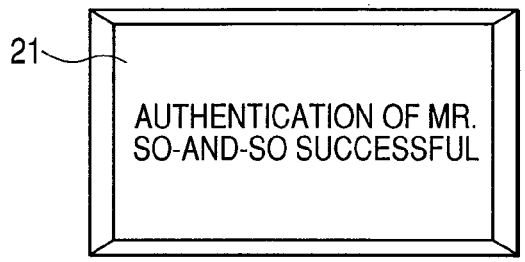
FIG. 15 is a drawing showing a fourth guide screen displayed on the biometric device when authentication succeeded in the first embodiment of this invention.

If authorization succeeded in step S10, then the biometric device 21 displays the fourth guide screen shown in FIG. 15 on the liquid crystal display substrate 4 (S16). The biometric device 21 at this time keeps the near-infrared ray light source 70 turned off and the backlight source 7 turned on. The biometric device 21 simultaneously notifies the user that authorization succeeded by a method such as sounding one beep tone, which is different from the method for notifying that authorization failed. The user is in this way notified that authorization succeeded while the user's finger is still placed on the biometric device 21.

The biometric device 21 then terminates the applicable processing.

FIG. 15 is a drawing showing the fourth guide screen displayed on the biometric device 21 when authentication succeeded in the first embodiment of this invention.

The biometric device 21 notifies the user that authorization succeeded by display a fourth guide screen. The fourth guide screen may also display the identifier of the user whose authentication was successful.

In the first embodiment of this invention, the detection position for light output from the subject 1 is changed by controlling the display screen from the liquid crystal display substrate 4. A biometric device 21 can be achieved by adding a PD array 8 made up of line sensors rather than two-dimensional image sensors on the back surface of the liquid crystal display screen mounted in the information terminal. The biometric device 21 of the first embodiment of this invention can therefore be made smaller and at a lower cost than the biometric device of the related art that uses two-dimensional image sensors.

Utilizing the silicon process technology of the known art allows a PD array 8 that is highly sensitive to near-infrared light to easily be produced. This technology improves the signal-to-noise (SN) ratio of the captured image and therefore boosts the authentication accuracy in the biometric device 21 of the first embodiment of this invention.

In the first embodiment of this invention, the near-infrared ray light source 70 is inside the biometric device 21 (liquid crystal section contained in the information terminal). However this near-infrared ray light source 70 may be outside the biometric device. The near-infrared ray light source 70 may in other words be installed in any location provided that near-infrared light irradiates onto the subject 1.

Second Embodiment

Figure 16:
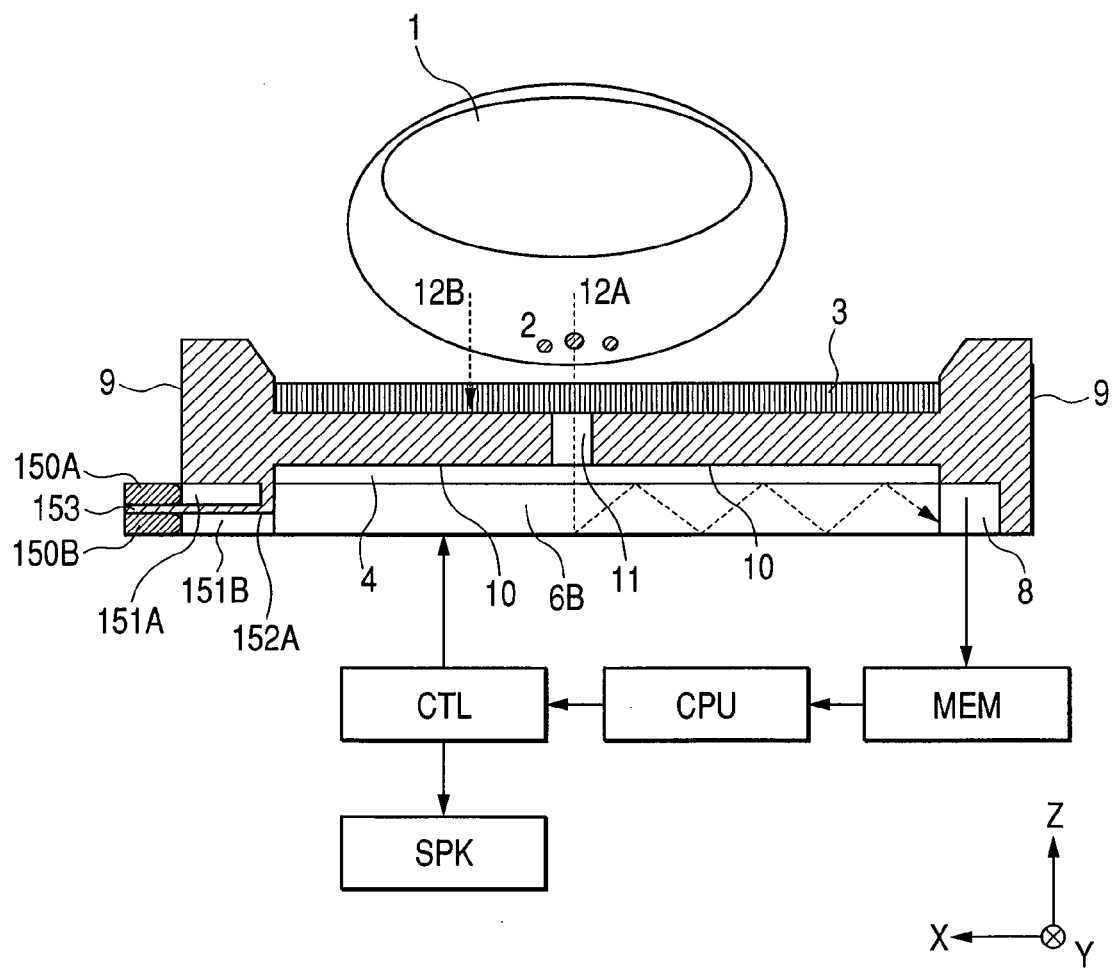
FIG. 16 is a drawing for showing the structure of the biometric device of the second embodiment of this invention.

FIG. 16 is a drawing for showing the structure of the biometric device of the second embodiment of this invention.

Most of the structure of the biometric device 21 of the second embodiment of this invention is identical to the biometric device of the first embodiment of this invention. Therefore the same reference numerals are assigned and a description is omitted in sections where the structure is identical.

In the biometric device 21 of the second embodiment, the near-infrared ray light source 150A is installed on one side surface of the light diffusion plate 151A along the X-axis. The light guide plate 6 is installed on the other side surface of the light diffusion plate 151A along the X-axis.

The near-infrared ray light source 150B is installed in the same way on one side surface of the light diffusion plate 151B along the X-axis. The light guide plate 6 is installed on the other side surface of the light diffusion plate 150B along the X-axis.

The near-infrared ray light source 150A and the near-infrared ray light source 150B are stacked (laminated) at a position along the Z-axis. The light diffusion plate 151A and the light diffusion plate 151B are stacked (laminated) at a position along the Z-axis. A partition wall 153 is installed between the near-infrared ray light source 150A and the near-infrared ray light source 150B; and between the light diffusion plate 151A and the light diffusion plate 151B.

This partition wall 153 is identical to the partition wall 73 contained in the biometric device 21 of the first embodiment, and prevents light from diffusing along the Z-axis.

A partition wall 152 is also installed between either the light diffusion plate 151A and the light guide plate 6, or the light diffusion plate 151B and the light guide plate 6. A partition wall 152A is placed between the light diffusion plate 151A and the light guide plate 6 in this drawing. If the partition wall 152A is not installed then a partition wall 152B is installed between the light diffusion plate 151B and the light guide plate 6.

The partition walls 152A and 152B are identical to the partition wall 73 contained in the biometric device 21 of the first embodiment. The partition walls 152A and 152B prevent light from diffusing onto the light guide plate 6.

The near-infrared ray light sources 150A and 150B are identical to the near-infrared ray light source 70 contained in the biometric device 21 of the first embodiment. The light diffusion plate 151A and the light diffusion plate 151B are identical to the light diffusion plate 5 contained in the biometric device 21 of the first embodiment.

The light diffusion plate 151B diffuses uniformly near-infrared light emitted from the near-infrared ray light source 150B, onto the X-Y planes. The near-infrared light diffused by the light diffusion plate 151B is then irradiated onto the surface of the light guide plate 6.

The light diffusion plate 151A in the same way uniformly diffuses the near-infrared light emitted from the near-infrared ray light source 150A, onto the X-Y planes. The white light diffused by the light diffusion plate 151A is then irradiated onto the edge of the light guide plate 6. In the drawing, however, the near-infrared light diffused by light diffusion plate 151A is blocked by the partition wall 152A, and does not irradiate onto the edge of the light guide plate 6.

If the near-infrared ray light source 150B is turned off, then no near-infrared light from either the near-infrared ray light sources 150A and 150B is irradiated onto the edge of the light guide plate 6. The light guide plate 6 therefore guides the near-infrared light 12A output from the surface of the subject 1, onto the PD array 8.

On the other hand, if the near-infrared light source 150B is turned on, and also if the liquid crystal display substrate 4 is displaying a white mask image on the area directly above the applicable light guide plate 6, then the near-infrared light irradiates from the near-infrared ray light source 150B onto the edge of the light guide plate 6. The light guide plate 6 also uniformly diffuses the near-infrared light irradiated from light diffusion plate 151B, along the X-axis. Moreover, among the diffused near-infrared light, the light guide plate 6 outputs the near-infrared light scattered by the reflective dots along the Z-axis. The light guide plate 6 in this way irradiates the near-infrared light onto the subject 1.

The light guide plate 6 in this embodiment includes a function to irradiate near-infrared light onto the subject 1, and a function to guide near-infrared light onto the PD array 8. The light guide plate 6 moreover contains a function to irradiate backlight onto the liquid crystal display substrate 4.

Figure 17:
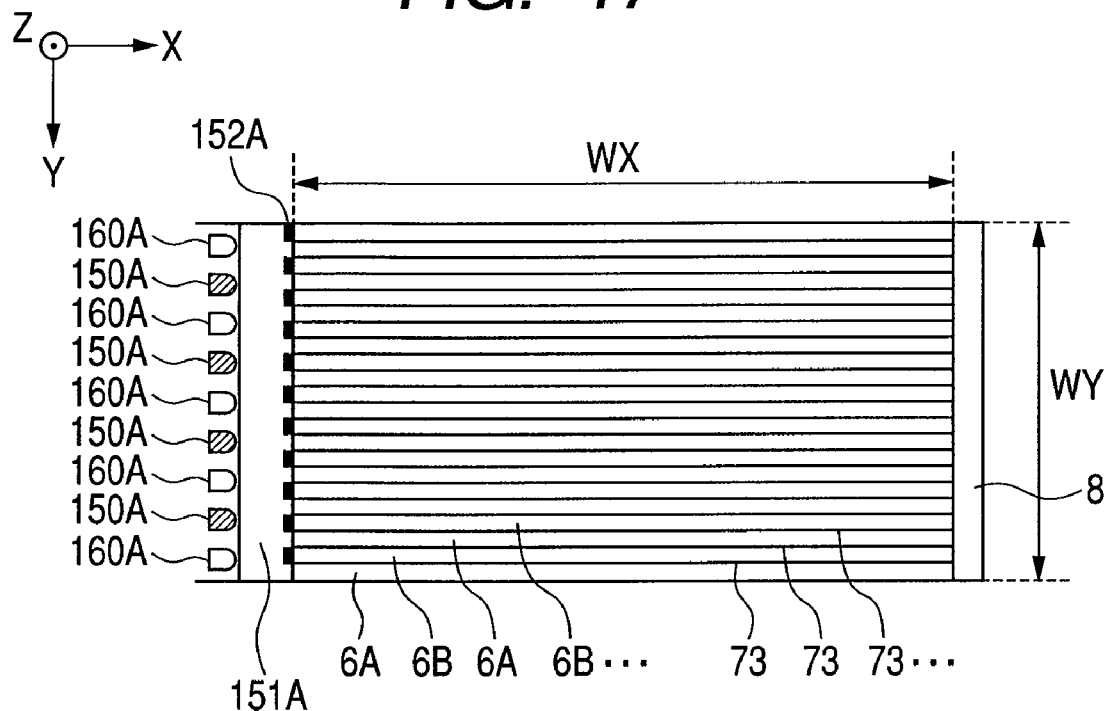
FIG. 17 is a drawing for showing the structure of the biometric device of the second embodiment of this invention.

FIG. 17 is a drawing showing the structure of the biometric device 21 of the second embodiment of this invention.

This drawing shows the placement of the near-infrared ray light source 150A, light diffusion plate 151A, backlight source 160A, and the light guide plates 6A and 6B.

A light guide plate 6A and light guide plate 6B are alternately installed directly below the display area of the liquid crystal display substrate 4. In this embodiment, the light guide plate 6 is subdivided into either a light guide plate 6A or a light guide plate 6B.

There is no partition wall 152A between the light guide plate 6A and the light diffusion plate 151A. A partition wall 152A is however installed between the light guide plate 6B and the light diffusion plate 151A. A partition wall 73 is installed between the light guide plate 6A and the light guide plate 6B.

A light diffusion plate 151A is installed on one side surface of the light guide plates 6A and 6B that are arrayed along the X-axis. A PD array 8 is installed on other side surface of the 6A and 6B arrayed along the X-axis. The near-infrared ray light source 150A and the backlight source 160A are installed on the side surface of the light diffusion plate 151A.

The light diffusion plate 151A uniformly diffuses the near-infrared light emitted from the near-infrared ray light source 150A and the white light emitted from the backlight source 7 onto the X-Y planes. The white light and the near-infrared light diffused by the light diffusion plate 151A is then irradiated onto the edge of the light guide plate 6. The near-infrared light and the white light diffused by the light diffusion plate 151A on the other hand, does not irradiate onto the edge of the light guide plate 6B.

The light guide plate 6A uniformly diffuses the near-infrared light and white light irradiated from the light diffusion plate 151A along the X-axis. Among this diffused near-infrared light and white light, the light guide plate 6A outputs the near-infrared light and white light scattered by the reflective dots, along the Z-axis. The light guide plate 6A in this way irradiates backlight onto the liquid crystal display substrate 4 when the liquid crystal display substrate 4 is displaying characters and images. The light guide plate 6A moreover irradiates near-infrared light onto the subject 1.

During image capture on the other hand, the near-infrared light output from the surface of the subject 1, transmits through the non-mask section 11 of the mask image displayed on the liquid crystal display substrate 4, and irradiates onto the surface of the light guide plate 6B. After the near-infrared light irradiated from the surface of the applicable light guide plate 6B is scattered by the reflective dots, and the light guide plate 6B guides the light along the X-axis. The light guide plate 6B irradiates the near-infrared light input from the surface of the applicable light guide plate 6B, into the PD array 8. The PD array 8 then detects the near-infrared light that was input from the light guide plate 6B. The PD array 8 detects the near-infrared light irradiated from the light guide plate 6 in parallel at each light guide plate 6.

Figure 18:
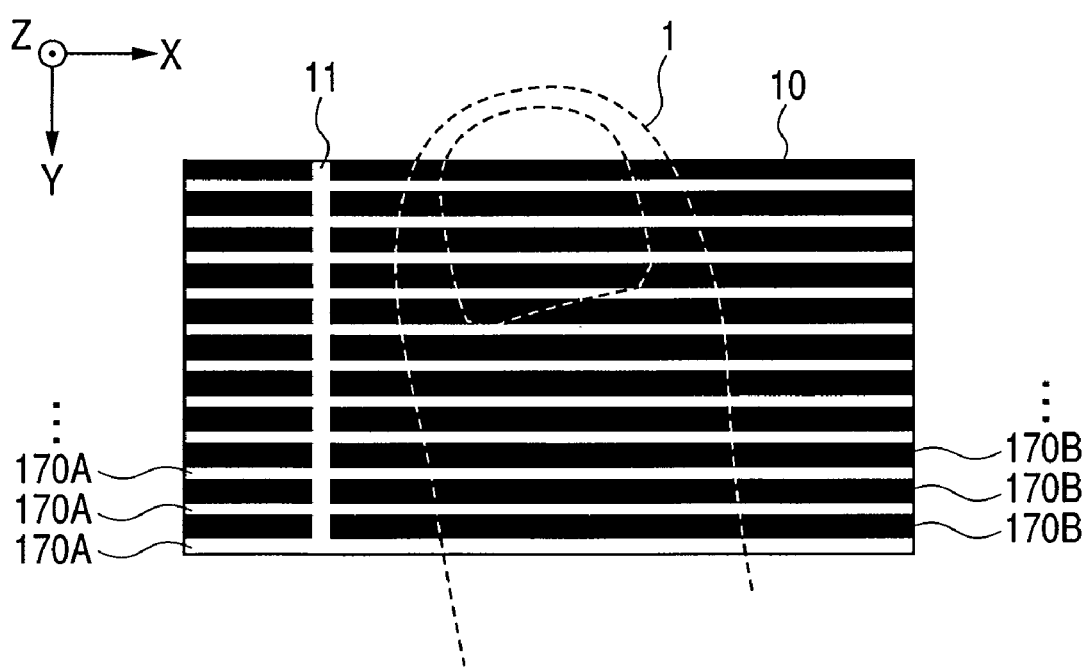
FIG. 18 is a drawing showing an example of the mask image displayed on the liquid crystal display substrate of the biometric device of the second embodiment of this invention.

FIG. 18 is a drawing showing an example of the mask image displayed on the liquid crystal display substrate 4 of the biometric device 21 of the second embodiment of this invention.

The mask image is displayed during image capture so the near-infrared ray light source 150A is turned on, and the backlight source 160A is turned off.

The mask image includes the near-infrared ray irradiation section 170A and the display-detector section 170B.

The near-infrared ray irradiation section 170A is an area directly above the light guide plate 6A and is displayed in white. The near-infrared light irradiated from the light guide plate 6A therefore transmits through the near-infrared ray irradiation section 170A and irradiates onto the subject 1.

The near-infrared light irradiated onto the subject 1 repeatedly transmits through and scatters in the interior of the subject 1. A portion of the near-infrared light irradiated onto the subject 1 is then output from the surface of the subject 1.

The display-detector section 170B is an area formed directly above the light guide plate 6B. The display-detector section 170B includes a mask section 10 and a non-mask section 11. The mask section 10 is displayed in black. The non-mask section 11 is displayed in white.

The mask section 10 blocks a portion of the near-infrared light emitted from the surface of the subject 1 which does not irradiate onto the surface of the light guide plate 6B. On the other hand, a portion of the near-infrared light emitted from the surface of the subject 1 irradiates onto the light guide plate 6B after transmitting through the non-mask section 11, and is detected by the PD array 8.

The biometric device 21 moves the non-mask section 11 in sequence along the X-axis during image capture. The biometric device 21 in this way moves the non-mask section 11 to all positions along the X-axis. The PD array 8 then measures the input light intensity at the respective positions where the non-mask section 11 was moved.

The central processing unit CPU generates two-dimensional images (first capture image) based on the input light intensity measured by the PD array 8. The vein 2 pattern of the subject 1 is drawn in an area on the first capture image corresponding to the light guide plate 6B.

Figure 19:
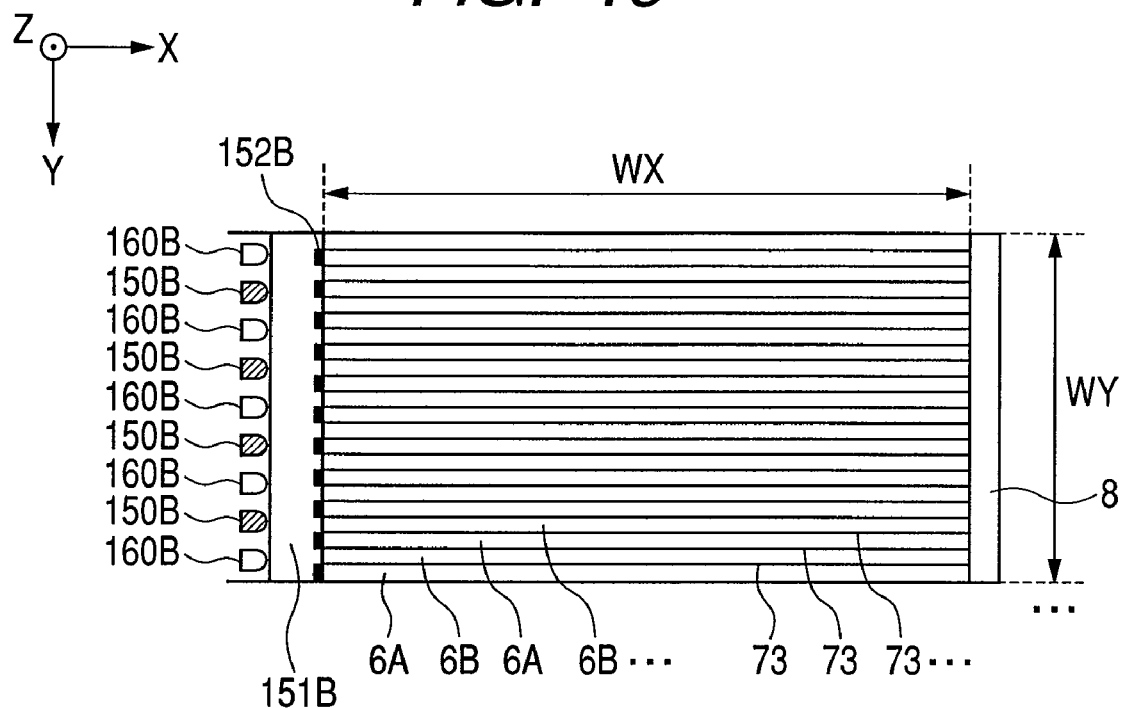
FIG. 19 is a drawing showing the structure of the biometric device of the second embodiment of this invention.

FIG. 19 is a drawing showing the structure of the biometric device 21 of the second embodiment of this invention.

This drawing shows the placement of the near-infrared ray light source 150B, light diffusion plate 151B, background light source 160B, and the light guide plates 6A and 6B.

A partition wall 152B is installed between the light guide plate 6A and the light diffusion plate 151B. However, there is no partition wall 152B installed between the light guide plate 6B and the light diffusion plate 151B. A partition wall 73 is installed between the light guide plate 6B and the light guide plate 6A.

A light diffusion plate 151B is installed on one side surface along the X-axis of the light guide plates 6A and 6B. A PD array 8 is installed on the other side surface along the X-axis of the light guide plates 6A and 6B. A near-infrared ray light source 150B and a backlight source 160B are installed on the side surface of the light diffusion plate 151B.

The light diffusion plate 151B uniformly diffuses the near-infrared light emitted from the near-infrared ray light source 150B and the white light emitted from the backlight source 7 onto the X-Y planes. The near-infrared light and the white light diffused by the light diffusion plate 151B are then irradiated onto the edge of the light guide plate 6B. The near-infrared light and the white light diffused by the light diffusion plate 151B on the other hand does not irradiate onto the edge of the light guide plate 6A.

The light guide plate 6B uniformly diffuses the near-infrared light and the white light input from the light diffusion plate 151B along the X-axis. Moreover, among this diffused near-infrared light and white light, the light guide plate 6B outputs the near-infrared light and white light scattered by the reflective dots is output along the Z-axis. The light guide plate 6 in this way irradiates a backlight onto the liquid crystal display substrate 4 when the liquid crystal display substrate 4 is displaying images and characters. The light guide plate 6B in this way irradiates near-infrared light onto the subject 1 during capture of the image.

During image capture on the other hand, the near-infrared light output from the surface of the subject 1, transmits through the non-mask section 11 of the mask image displayed on the liquid crystal display substrate 4, and irradiates onto the surface of the light guide plate 6A. After the near-infrared light input from the surface of the applicable light guide plate 6A is scattered by the reflected dots, the light guide plate 6A guides it along the X-axis. The light guide plate 6A in this way, irradiates the near-infrared light input from the surface of the applicable light guide plate 6A, into the PD array 8. The PD array 8 then detects the near-infrared light that was input from the light guide plate 6B. The PD array 8 detects the near-infrared light irradiated from the light guide plate 6A in parallel at each light guide plate 6A.

Figure 20:
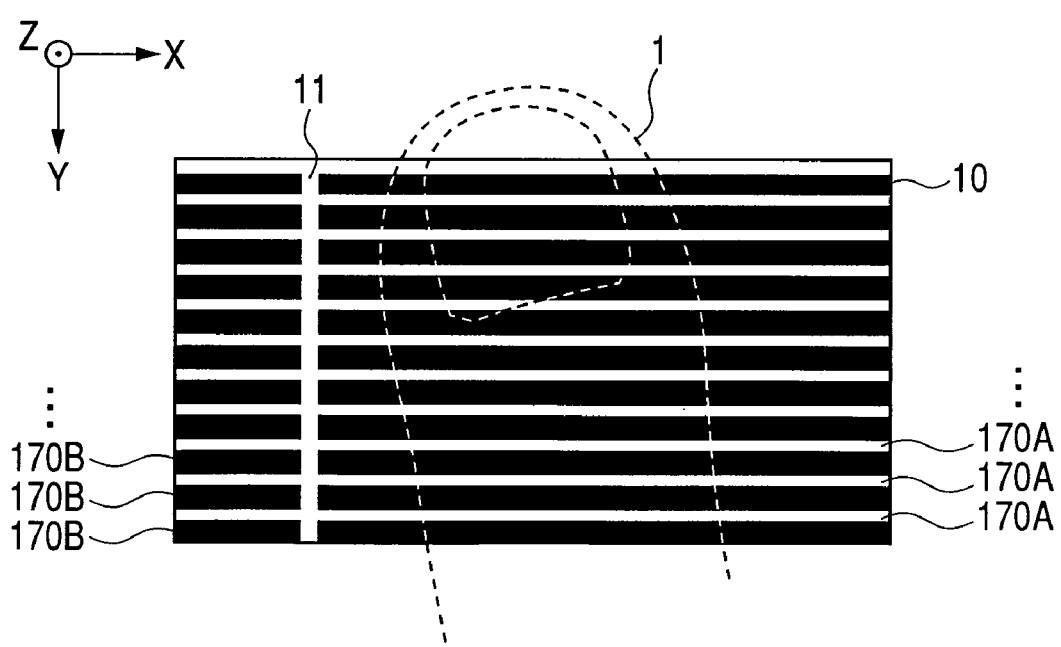
FIG. 20 is a drawing showing an example of the mask image displayed on the liquid crystal display substrate of the biometric device of the second embodiment of this invention.

FIG. 20 is a drawing showing an example of the mask image displayed on the liquid crystal display substrate 4 of the biometric device 21 of the second embodiment of this invention.

The mask image is displayed during capture of the image. Therefore, during that state, the near-infrared ray light source 150B is turned on and the backlight source 160B is turned off.

The mask image includes the near-infrared ray irradiation section 170A and the display-detector section 170B. In the mask image shown in FIG. 20, the near-infrared ray irradiation section 170A and the display-detector section 170B are interchanged compared to the mask image shown in FIG. 18.

The near-infrared ray irradiation section 170A is an area directly above the light guide plate 6B and is displayed in white. The near-infrared light irradiated from the light guide plate 6B therefore transmits through the near-infrared ray irradiation section 170A and irradiates onto the subject 1.

The near-infrared light irradiated onto the subject 1 repeatedly transmits through and scatters in the interior of the subject 1. A portion of the near-infrared light irradiated onto the subject 1 is then output from the surface of the subject 1.

The display-detector section 170B is an area formed directly above the light guide plate 6A. The display-detector section 170B includes a mask section 10 and a non-mask section 11. The mask section 10 is displayed in black. The non-mask section 11 is displayed in white.

The mask section 10 blocks a portion of the near-infrared light emitted from the surface of the subject 1 which does not irradiate onto the surface of the light guide plate 6A. On the other hand, a portion of the near-infrared light emitted from the surface of the subject 1 irradiates onto the surface of the light guide plate 6A after transmitting through the non-mask section 11, and is detected by the PD array 8.

The biometric device 21 moves the non-mask section 11 in sequence along the X-axis during image capture. The biometric device 21 in this way moves the non-mask section 11 to all positions along the X-axis. The PD array 8 then measures the input light intensity at the respective positions where the non-mask section 11 was moved.

The central processing unit CPU generates two-dimensional images (second capture image) based on the input light intensity measured by the PD array 8. The vein 2 pattern of the subject 1 is drawn in an area on the second capture image corresponding to the light guide plate 6A.

The central processing unit CPU forms a third capture image by making a composite of the first capture image and the second capture image. The central processing unit CPU then performs authentication based on the third capture image that was formed.

In the present embodiment, the backlight sources 160A and 160B may be turned on when the liquid crystal display substrate 4 is displaying images and characters.

In the second embodiment of this invention, the position for irradiating the near-infrared light on the subject 1 is near the position for detecting the infrared light output from the subject 1. The biometric device 21 can therefore capture a two-dimensional image with minimal irregularities in the light intensity. The biometric device 21 can therefore provide enhanced authentication accuracy.

Third Embodiment

Figure 21:
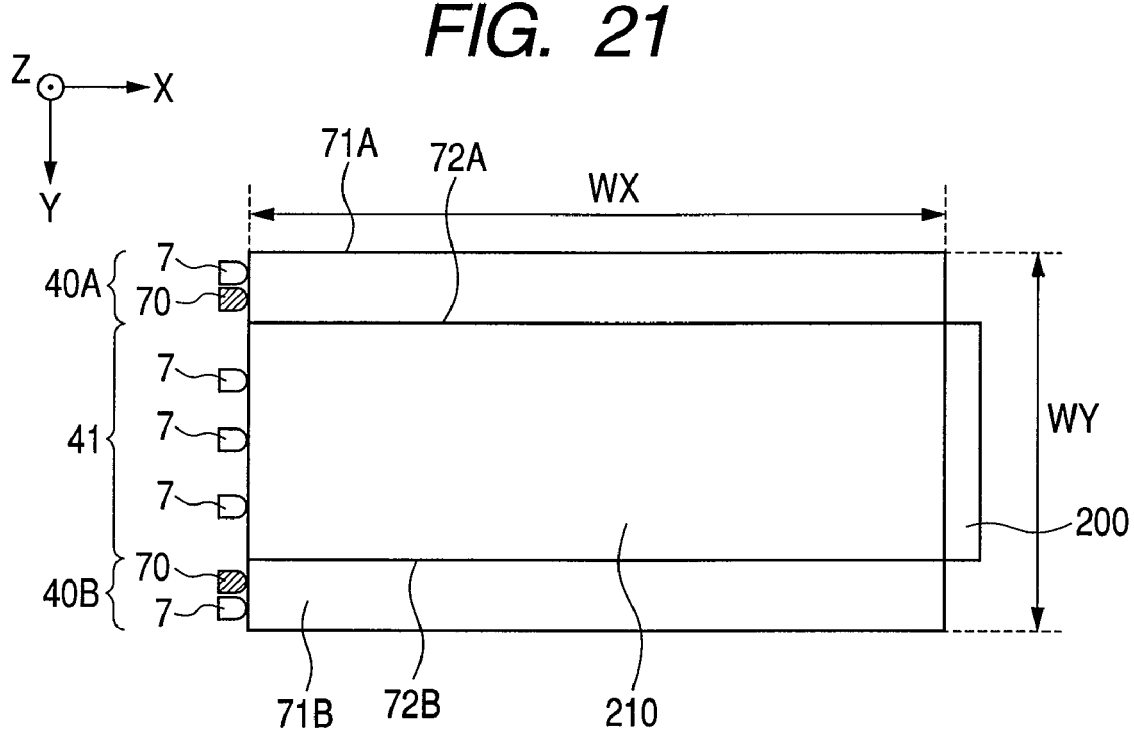
FIG. 21 is a drawing for showing the structure of the biometric device of the third embodiment of this invention.

FIG. 21 is a drawing for showing the structure of the biometric device 21 of the third embodiment of this invention.

This drawing shows the placement of the light diffusion plate 5, the light guide plate 210, the backlight source 7, the PD 200, the light guide plates 71A, 71B and the near-infrared ray light source 70.

Most of the structure of the biometric device 21 of the third embodiment of this invention is identical to the biometric device of the first embodiment of this invention. The same reference numerals are therefore assigned and a description is omitted in sections where the structure is identical.

The biometric device 21 of the third embodiment contains a single light guide plate 210 instead of the light diffusion plate 5 and the multiple light guide plates 6.

Aside from the point that the size is different, the light guide plate 210 is identical to the light guide plate 6 in the biometric device 21 of the first embodiment of this invention. The light guide plate 210 uniformly diffuses the white light emitted from the backlight source 7 along the X-Y plane and not along the X-axis.

After the near-infrared light input from the surface of the applicable light guide plate 210, is scattered by the reflective dots, the light guide plate 210 guides it to the X-Y plane. The light guide plate 210 inputs the near-infrared light input from the surface of the applicable light guide plate 210 to the PD 200.

The biometric device 21 of the third embodiment contains a PD 200 instead of the PD array 8. The PD 200 includes an element containing a single long photo sensor along the Y-axis, for detecting near-infrared light input from the light guide plate 210. The PD 200 is sensitive to light from the entire side surface of light guide plate 210.

Figure 22:
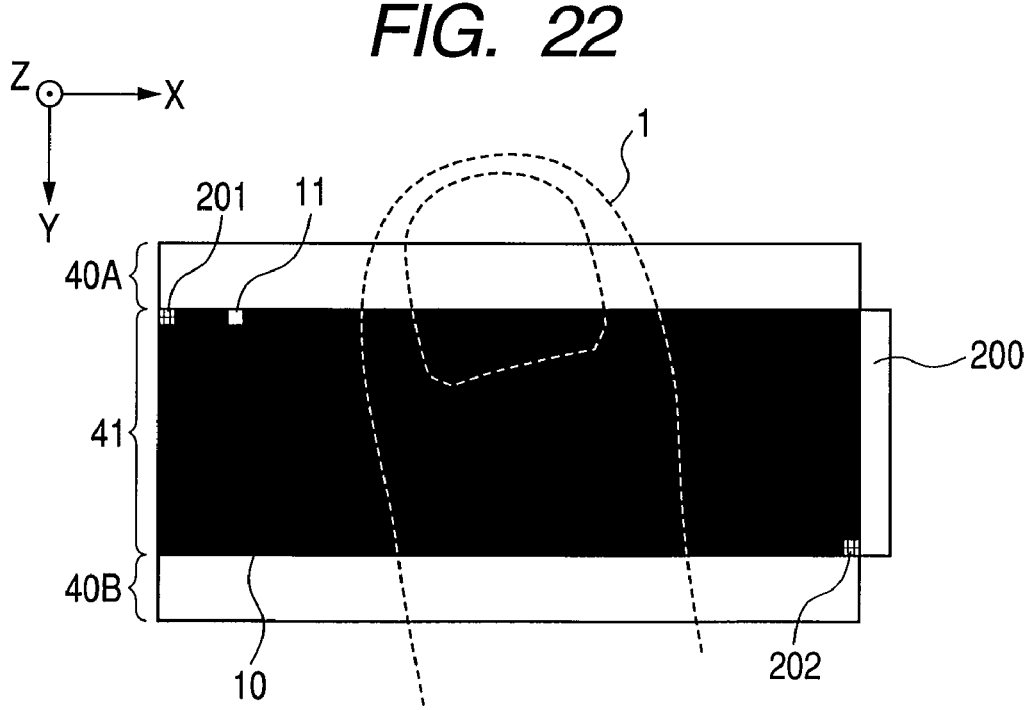
FIG. 22 is a drawing showing the mask image displayed on the liquid crystal display substrate of the biometric device of the third embodiment of this invention.

FIG. 22 is a drawing showing the mask image displayed on the liquid crystal display substrate 4 of the biometric device 21 of the third embodiment of this invention.

Aside from the point that the non-mask section 11 of the mask image is made up of only a single dot, the third embodiment is identical to the mask image of the first embodiment (FIG. 4).

During image capture, the biometric device 21 moves each dot (non-mask section 11) position in sequence along the X-axis from the start position 201. When a dot reaches one edge of the X-axis, the biometric device 21 shifts that applicable dot along the Y-axis by a size equal to one dot, and also shifts that dot towards the other edge of the X-axis. The biometric device 21 then repeats this dot movement until the dot reaches the end position 202.

The biometric device 21 in this way moves the dot to all areas in the display-detector section 41. The PD 200 then measures the input light intensity at all positions where the dot was moved.

The central processing unit CPU forms a two-dimensional image (captured image) based on the intensity of the light input by the PD array 200. The CPU draws the vein 2 pattern of the subject 1 on the captured image.

In the third embodiment of this invention, the biometric device 21 moves single dots to all areas contained in the display-detector section 41. This movement increases the time required for image capture.

However the biometric device 21 of the third embodiment of this invention may include a PD 200 made up of a single element instead of a PD array 8 that uses multiple elements. The biometric device 21 can therefore be produced for a low cost.

This invention can be utilized in biometric devices for identifying individuals based on biologic information.

What is claimed is:

1. A device comprising:
   a first light source which emits light to be irradiated onto a subject;
   a first light guide unit which receives light radiated from the subject and which outputs received light;
   a second light guide unit for guiding and irradiating the light emitted from the first light source onto the subject;
   a sensor unit which detects light outputted from the first light guide unit as a signal;
   a liquid crystal display unit positioned between the subject and the first light guide unit;
   a control unit which controls the liquid crystal display unit to display a mask image formed by a mask section and a non-mask section, and
   a signal processing unit for processing said signal detected by the sensor unit,
   wherein the control unit controls the liquid crystal display unit so that the non-mask section is formed in an area of the liquid crystal display unit corresponding to a surface region of the second light guide unit and corresponding to a part of a surface region of the first light guide unit, and controls the liquid crystal display unit so that a position of the non-mask section corresponding to a part of the surface region of the first light guide unit changes,
   wherein the signal processing unit generates an image including a biometric pattern of the subject based on the signal detected by the sensor unit from changes in the position of the non-mask section corresponding to a part of the surface region of the first light guide unit.

2. The device according to claim 1, wherein the signal processing unit performs a comparison between the image and a preliminary stored image and performs identification of the subject according to a result of the comparison.

3. The device according to claim 1,
   wherein the first light guide unit includes multiple light guide sections;
   wherein the sensor unit includes multiple sensor elements,
   wherein the sensor elements are installed at an edge of the light guide sections and correspond to respective ones of the light guide sections, and
   wherein the light outputted from each of the light guide sections is detected as the signal.

4. The device according to claim 3, wherein a light shield unit is installed between adjacent light guide sections.

5. The device according to claim 3, wherein the control unit controls the display on the liquid crystal display unit to change input positions where light is input to each of the light guide sections.

6. The device according to claim 4, wherein the control unit controls the liquid crystal display unit so that the input positions for the light at a particular point in time for adjacent light guide sections are not along an axis perpendicular to an axis of any of the adjacent light guide sections.

7. The device according to claim 1, further comprising a second light source,
   wherein the first light guide unit and the second light guide unit guide the light emitted from the second light source and irradiate the liquid crystal display unit.

8. The device according to claim 7, further comprising a third light guide unit for guiding and irradiating the light emitted from the second light source, onto the first light guide unit.

9. The device according to claim 3,
   wherein the first light source includes multiple light emitting elements which are to be switched to emit light,
   wherein the light guide sections correspond with the light emitting elements, and
   wherein the signal processor unit forms an image based on the signal detected by the optical sensor element detecting light outputted from the edge of the light guide section corresponding to the light emitting element which does not emit light.

10. An information terminal comprising:
    a first light source which emits light to be irradiated onto a subject;
    a first light guide unit which receives light radiated from the subject and which outputs received light;
    a second light guide unit for guiding and irradiating the light emitted from the first light source onto the subject;
    a sensor unit which detects light outputted from the first light guide unit as a signal;

a liquid crystal display unit positioned between the subject and the first light guide unit;

a control unit which controls the liquid crystal display unit to display a mask image formed by a mask section and a non-mask section, and a signal processing unit for processing said signal detected by the sensor unit, wherein the control unit controls the liquid crystal display unit so that the non-mask section is formed in an area of the liquid crystal display unit corresponding to a surface region of the second light guide unit and corresponding to a part of a surface region of the first light guide unit, and controls the liquid crystal display unit so that a position of the non-mask section corresponding to a part of the surface region of the first light guide unit changes, wherein the signal processing unit generates an image including a biometric pattern of the subject based on the signal detected by the sensor unit from changes in the position of the non-mask section corresponding to a part of the surface region of the first light guide unit.

11. The information terminal according to claim 10, wherein the signal processing unit performs a comparison between the image and a preliminary stored image and performs identification of the subject according to a result of the comparison.

12. The information terminal according to claim 10,
wherein the first light guide unit includes multiple light guide sections;
wherein the sensor unit includes multiple sensor elements,
wherein the sensor elements are installed at an edge of the light guide sections and correspond to respective ones of the light guide sections, and
wherein the light outputted from each of the light guide sections is detected as the signal.

13. The information terminal according to claim 10, further comprising a pair of electrodes which confirm the presence of the subject when both electrodes are in contact with the subject.

* * * * *